US008486336B2

(12) United States Patent
Kageyama et al.

(10) Patent No.: US 8,486,336 B2
(45) Date of Patent: Jul. 16, 2013

(54) MICROCHIP

(75) Inventors: Yasuhisa Kageyama, Kyoto (JP);
Youichi Aoki, Kyoto (JP)

(73) Assignee: Rohm Co., Ltd., Kyoto (JP)

( * ) Notice: Subject to any disclaimer, the term of this patent is extended or adjusted under 35 U.S.C. 154(b) by 713 days.

(21) Appl. No.: 12/424,913

(22) Filed: Apr. 16, 2009

(65) Prior Publication Data
US 2009/0263282 A1  Oct. 22, 2009

(30) Foreign Application Priority Data

| Apr. 18, 2008 | (JP) | 2008-109314 |
| May 12, 2008 | (JP) | 2008-125024 |
| Sep. 25, 2008 | (JP) | 2008-245648 |
| Oct. 28, 2008 | (JP) | 2008-277074 |

(51) Int. Cl.
*G01N 33/00* (2006.01)
*G01N 1/10* (2006.01)
*F04B 19/00* (2006.01)
*B01D 45/00* (2006.01)
*B01L 3/00* (2006.01)
*B01D 21/00* (2006.01)
*G01N 9/30* (2006.01)
*G01N 21/90* (2006.01)
*G01N 35/00* (2006.01)
*C12M 3/00* (2006.01)

(52) U.S. Cl.
USPC ............ 422/68.1; 422/72; 422/502; 422/504; 422/506; 422/533; 422/527; 435/286.7; 435/287.1; 435/288.5; 435/288.6; 435/290.2; 356/39; 356/427; 356/246; 436/45

(58) Field of Classification Search
USPC ............... 422/68.1, 502, 504, 506, 535, 527, 422/533, 72, 100; 435/286.7, 287.1, 288.5, 435/288.6, 290.2
See application file for complete search history.

(56) References Cited

U.S. PATENT DOCUMENTS

| 4,463,097 A | * | 7/1984 | Guigan | 436/45 |
| 4,469,793 A | * | 9/1984 | Guigan | 436/45 |
| 4,814,282 A | * | 3/1989 | Holen et al. | 436/165 |
| 4,883,763 A | * | 11/1989 | Holen et al. | 436/45 |
| 4,940,527 A | * | 7/1990 | Kazlauskas et al. | 204/401 |
| 7,312,611 B1 | * | 12/2007 | Harrison et al. | 324/453 |

(Continued)

FOREIGN PATENT DOCUMENTS

| JP | 60-238760 | 11/1985 |
| JP | 05-508709 | 12/1993 |

(Continued)

OTHER PUBLICATIONS

U.S. Appl. No. 12/467,404, filed May 18, 2009.

*Primary Examiner* — Bobby Ramdhanie
*Assistant Examiner* — Jennifer Wecker
(74) *Attorney, Agent, or Firm* — Fish & Richardson P.C.

(57) ABSTRACT

A microchip including a fluid circuit formed by a groove of a first substrate and a surface of a second substrate is provided. The fluid circuit includes a fluid retaining reservoir for containing a fluid. The fluid retaining reservoir includes a fluid outlet or outflow channel for allowing the fluid to flow out, and a partition dividing the fluid retaining reservoir into a first region including a fluid inlet for injecting a fluid into the fluid retaining reservoir and a second region including the fluid outlet or outflow channel. The partition includes at least one communication gate for allowing communication between the first region and the second region.

9 Claims, 12 Drawing Sheets

U.S. PATENT DOCUMENTS

| | | | |
|---|---|---|---|
| 2007/0243111 A1 * | 10/2007 | Momose | 422/100 |
| 2008/0056945 A1 | 3/2008 | Hattori | |
| 2008/0156079 A1 | 7/2008 | Momose et al. | |
| 2008/0296734 A1 | 12/2008 | Momose | |
| 2009/0084738 A1 | 4/2009 | Momose | |
| 2009/0098658 A1 | 4/2009 | Momose et al. | |
| 2009/0104077 A1 | 4/2009 | Momose | |
| 2009/0111675 A1 | 4/2009 | Yokogawa et al. | |
| 2009/0135407 A1 | 5/2009 | Kageyama et al. | |
| 2009/0142232 A1 | 6/2009 | Okada et al. | |
| 2009/0155125 A1 * | 6/2009 | Michiue et al. | 422/100 |
| 2009/0232708 A1 | 9/2009 | Yokogawa et al. | |

FOREIGN PATENT DOCUMENTS

| | | |
|---|---|---|
| JP | 2006-208183 A | 10/2006 |
| JP | 2006-313122 | 11/2006 |
| JP | 2007-017342 | 1/2007 |
| JP | 2007017342 A * | 1/2007 |
| JP | 2007-139480 | 6/2007 |
| JP | 2007-229631 | 9/2007 |
| JP | 2007-285792 | 11/2007 |
| JP | 2007-285968 | 11/2007 |
| WO | 2005/123242 A1 | 12/2005 |

* cited by examiner

MICROCHIP

BACKGROUND OF THE INVENTION

1. Field of the Invention

The present invention relates to a microchip useful as a μ-TAS (Micro Total Analysis System) or the like that is suitably used for such purposes as biochemical tests for DNA, protein, cell, immunity, and blood for example, chemical synthesis and environmental analysis. More specifically, the present invention relates to a microchip having therein a fluid retaining reservoir for containing a fluid such as reagent to be mixed or reacted with a sample to be tested or analyzed for example.

2. Description of the Background Art

In recent years, in the fields of medical care, health, food, and drug discovery for example, sensing, detection or quantitation of biological substances such as DNA (Deoxyribo Nucleic Acid), enzyme, antigen, antibody, protein, virus, and cell as well as chemical substances has become increasingly important, and various biochips and micro chemical chips (they are hereinafter referred to collectively as microchip) with which the above-described substances can be easily and conveniently measured have been proposed. The microchip can be used to allow a series of experimental and analytical operations usually performed in a laboratory to be conducted within the chip of several centimeters per side and approximately several millimeters to one centimeter in thickness. The microchip accordingly provides many advantages that the amounts of samples and reagents to be used are very small, the cost is low, the reaction rate is high, high throughput test can be conducted, and the test results can be immediately obtained at the site where the sample was taken, for example. The microchip is suitably used for biochemical tests such as blood test for example.

The microchip commonly includes therein "fluid circuit" that is a fluid channel network constituted of portions (chambers) where a specific treatment is performed on a fluid, and a fine fluid channel appropriately connecting these portions. In the test and analysis of a sample (such as blood or a specific component of the blood for example in the case of the blood test) by means of a microchip having therein such a fluid circuit as described above, the fluid circuit is used to perform various fluid treatments such as measurement of a sample introduced into the fluid circuit, measurement of a reagent to be mixed with the sample, and mixing of the sample with the reagent. The various fluid treatments can be performed by applying a centrifugal force in an appropriate direction to the microchip.

A microchip having a fluid circuit in which a reagent to be mixed or reacted with a sample or a specific component in the sample is contained and retained in advance, namely so-called reagent-contained microchip, has been known (see for example Japanese Patent Laying-Open No. 2007-017342, U.S. Pat. No. 4,883,763 and Japanese Patent Laying-Open No. 2007-229631). The reagent-contained microchip usually includes, as a part of the fluid circuit of the microchip, one or a plurality of reagent retaining reservoirs for retaining a reagent. Further, the reagent-contained microchip usually has a reagent inlet formed in one of the surfaces of the microchip and extending through to the reagent retaining reservoir for injecting a reagent into the reagent retaining reservoir. The reagent-contained microchip is produced in the following manner. A reagent is injected through the reagent inlet, and thereafter a sealing label (seal) or the like for example is bonded to the surface of the microchip to seal the reagent inlet. The microchip is shipped in this state for use.

Regarding such a reagent-contained microchip, in order to perform a test and analysis for a sample with high precision, degradation of the contained reagent has to be sufficiently suppressed or prevented from the time when the microchip is produced (when the reagent is injected) to the time when the microchip is actually used. Further, the reagent should be sufficiently suppressed or prevented from flowing out of the reagent retaining reservoir, which could be caused for example by impact on the microchip or by an increase of the internal pressure of the reagent retaining reservoir during transportation and delivery of the microchip for example. This is for the following reason. If the reagent deteriorates or flows out of the reagent retaining reservoir, the reagent and the sample (or a specific component contained in the sample) will not properly react, or the microchip contains no reagent to be mixed with the sample (or a specific component contained in the sample) when the sample is tested and analyzed, or the reagent and the sample (or a specific component contained in the sample) are not mixed at an appropriate ratio, which could result in the possibility that accurate and highly reliable test and analysis results cannot be obtained.

U.S. Pat. No. 4,883,763 and Japanese Patent Laying-Open No. 2007-139480 for example each disclose a reagent-contained microchip in which a reagent contained in the microchip is sealed so that deterioration of the reagent and unintended outflow of the reagent can be prevented until the microchip is used. FIG. 21 is a plan view showing an example of the reagent-contained microchip disclosed in U.S. Pat. No. 4,883,763. In the microchip shown in FIG. 21, chambers 96 and 98 retaining a reagent are sealed containers slidable with respect to a substrate and each having an openable portion 10 where an opening can be made. At respective positions opposite to chambers 96 and 98, spike or needle-shaped opening means 12 are provided. This structure allows the reagent to be sealed in chambers 96 and 98 until the microchip is used. When the microchip is used, this structure allows the reagent to flow out through an opening made in openable portion 10 by opening means 12 as a result of application of a centrifugal force in $F_0$ direction shown in FIG. 21.

Although the above-described structure is highly effective at preventing deterioration of the reagent and unintended outflow of the reagent, there is a possibility that the whole amount of the reagent does not flow out from the hole made by opening means 12. If some of the reagent remains in chamber 96 or 98, application of a centrifugal force in a subsequent fluid treatment process could cause the remaining reagent to flow out again to adversely affect mixing or reaction of the reagent with a sample or adversely affect the results of the test and analysis of a fluid mixture of a sample and the reagent.

Further, the microchip disclosed in U.S. Pat. No. 4,883,763 has a problem that the structure of the reagent retaining reservoir (chamber) is very complicated and thus the reservoir is not easy to produce. Specifically, it is necessary to provide a window in the container in which the reagent is sealed and further attach a film or the like to the window so that a hole can be formed with a needle or the like, as openable portion 10. It is also necessary to slidably dispose the container on the substrate. Further, since the microchip has a movable portion (slidable container), the microchip lacks operational stability. For example, when an operational failure of the movable portion occurs, the reagent may not flow out.

Japanese Patent Laying-Open No. 2007-229631 discloses a microreactor in which a liquid such as reagent or sample can be surely stopped at a desired position and the liquid can be surely restarted from the position where the liquid is stopped. The disclosed microreactor includes a water repellant valve constituted of an upstream side connection hole having a smaller cross-sectional area than the cross-sectional area of an upstream side flow channel, a downstream side connection hole having a smaller cross sectional area than the cross-sectional area of a downstream side flow channel, and a connection hole communicating portion allowing communication between the upstream side connection hole and the downstream side connection hole and having a continuously varying cross-sectional area. On the two opposing ends of a storage portion where a reagent or sample is stored, the water repellant valves are provided respectively (see in particular FIGS. 3 and 5 of Japanese Patent Laying-Open No. 2007-229631).

Even if the water repellant valve having the above-described structure is provided, impact or an increase of the internal pressure for example during transportation and delivery of the microchip could cause the liquid to move from a predetermined position or flow out. Thus, there still has been room for improvement of the ability to retain a fluid such as reagent (ability to prevent outflow or leakage of the fluid).

SUMMARY OF THE INVENTION

The present invention has been made to solve the above-described problems, and an object of the invention is to provide a microchip including therein a fluid retaining reservoir having a relatively simplified structure for containing a fluid such as reagent. In the microchip having therein the fluid retaining reservoir, the reagent can be retained in a nearly sealed state and, even if an external impact is applied to the microchip or an internal pressure of the fluid retaining reservoir increases, for example, the reagent can be effectively prevented from outflowing from the fluid retaining reservoir.

Specifically, the present invention is a microchip including: a first substrate and a second substrate, the first substrate being superposed on the second substrate and having a surface with a groove; and a fluid circuit composed of a cavity defined by the groove of the first substrate and a surface on the first substrate side of the second substrate. The fluid circuit includes a fluid retaining reservoir for containing a fluid. The first substrate has a fluid inlet for injecting a fluid into the fluid retaining reservoir, and the fluid inlet is a through opening extending through the first substrate from a surface opposite to the surface with the groove of the first substrate to the fluid retaining reservoir. The fluid retaining reservoir includes: a fluid outlet or outflow channel for allowing the fluid to flow out; and a partition dividing the fluid retaining reservoir into a first region including the fluid inlet and a second region including the fluid outlet or outflow channel. The partition includes at least one communication gate for allowing communication between the first region and the second region.

Preferably, the partition includes two communication gates. In this case, preferably the two communication gates are disposed respectively at two opposing ends of the partition.

Preferably, a cross section, parallel to the surface with the groove of the first substrate, of at least a part of the partition has a substantially V shape or substantially U shape protruding toward the first region. Alternatively, preferably a cross section, parallel to the surface with the groove of the first substrate, of at least a part of the partition has a substantially V shape or substantially U shape protruding toward the second region.

The height of the communication gate at an end abutting on the first region and the height of the communication gate at an end abutting on the second region may be substantially equal to each other. Alternatively, the communication gate may have an upper inner wall inclining in such a manner that the height of the communication gate decreases from the first region toward the second region. "Upper" herein refers to the upper side when the first substrate is superposed on the second substrate.

Further, in the first region, a region adjacent to the communication gate may have an upper inner wall inclining in such a manner that, in the region adjacent to the communication gate, the height of the fluid retaining reservoir decreases toward the communication gate.

The microchip of the present invention having the above-described structure may be a liquid-reagent-contained microchip in which a liquid reagent is contained in a liquid reagent retaining portion that is a fluid retaining reservoir of the microchip. In this case, a liquid reagent inlet serving as a fluid inlet is sealed on the surface of the microchip on the side having the inlet (namely the surface of the first substrate) by attaching for example a sealing label or sealing seal.

The present invention is also a microchip including: a first substrate and a second substrate, the first substrate being superposed on the second substrate and having a surface with a groove; and a fluid circuit composed of a cavity defined by the groove of the first substrate and a surface on the first substrate side of the second substrate. The fluid circuit includes a fluid retaining reservoir that is a portion for retaining a fluid and includes a first outlet or first outflow channel for allowing the fluid to flow out; and a fluid containing reservoir that is a portion connected to the first outlet or first outflow channel for containing the fluid flowing out from the fluid retaining reservoir and includes a second outlet or second outflow channel for allowing the fluid to flow out.

In a preferred embodiment, the fluid retaining reservoir includes a first outflow channel for allowing the fluid to flow out, and the fluid containing reservoir includes a second outflow channel for allowing the fluid to flow out. In this case, preferably the second outflow channel extends in a direction different from the direction in which the first outflow channel extends.

In the case where the fluid containing reservoir includes a second outflow channel for allowing the fluid to flow out, preferably an end of the second outflow channel is connected to a measurement portion for measuring the fluid.

Preferably, the first substrate includes a fluid inlet for injecting a fluid into the fluid retaining reservoir. The fluid inlet is a through opening extending through the first substrate from a surface opposite to the surface with the groove of the first substrate to the fluid retaining reservoir. In this case, preferably the fluid retaining reservoir includes a partition dividing the fluid retaining reservoir into a first region having the fluid inlet and a second region having a first outlet or first outflow channel, and the partition includes at least one communication gate for allowing communication between the first region and the second region.

Preferably, the partition includes two communication gates. In this case, preferably the two communication gates are disposed respectively at two opposing ends of the partition.

Preferably, a cross section, parallel to the surface with the groove of the first substrate, of at least a part of the partition has a substantially V shape or substantially U shape protruding toward the first region. Alternatively, preferably a cross section, parallel to the surface with the groove of the first substrate, of at least a part of the partition has a substantially V shape or substantially U shape protruding toward the second region.

The height of the communication gate at an end abutting on the first region and the height of the communication gate at an end abutting on the second region may be substantially equal to each other. Alternatively, the communication gate may have an upper inner wall inclining in such a manner that the height of the communication gate decreases from the first region toward the second region. "Upper" herein refers to the upper side when the first substrate is superposed on the second substrate.

Further, in the first region, a region adjacent to the communication gate may have an upper inner wall inclining in such a manner that, in the region adjacent to the communication gate, the height of the fluid retaining reservoir decreases toward the communication gate.

The microchip of the present invention having the above-described structure may be a liquid-reagent-contained microchip in which a liquid reagent is retained in a liquid reagent retaining portion that is a fluid retaining reservoir of the microchip. In this case, a liquid reagent inlet serving as a fluid inlet is sealed on the surface of the microchip on the side having the inlet (namely the surface of the first substrate) by attaching for example a sealing label or sealing seal.

The present invention is also a microchip including: a first substrate and a second substrate, the first substrate being superposed on the second substrate and having a surface with a groove; and a fluid circuit composed of a cavity defined by the groove and a surface on the first substrate side of the second substrate. The fluid circuit includes a fluid retaining reservoir for retaining a fluid. The fluid retaining reservoir includes: a fluid outlet for allowing the fluid to flow out from the fluid retaining reservoir; and a partition dividing the fluid retaining reservoir into a first region where the fluid is introduced and a second region where the fluid outlet is included. The partition includes a communication gate for allowing communication between the first region and the second region. At least a part of the partition includes a curved portion formed of a wall in a shape of a curve as seen from a surface of the microchip.

Preferably the curved portion is formed of a wall in a shape of an arc protruding toward the second region. Preferably the arc has a radius of curvature of 2 to 5 mm.

Further, preferably a side surface of the partition abutting on the first region has an inclined surface inclined with respect to thickness direction of the microchip.

In a preferred embodiment, the partition is composed of a protrusion provided on a surface of the first substrate or the second substrate, and the communication gate is composed of a space defined between the protrusion and an opposite surface of the second substrate or the first substrate. In this case, preferably a surface of the protrusion forming the communication gate extends parallel or substantially parallel to the opposite surface of the second substrate or the first substrate. Further, preferably an angle between the surface of the first substrate or the second substrate having the protrusion provided thereon and forming the first region, and a side surface of the protrusion abutting on the first region, is an obtuse angle.

In another preferred embodiment, the partition is composed of respective protrusions provided on respective surfaces of the first substrate and the second substrate, and the communication gate is composed of a space defined between the protrusion provided on the surface of the first substrate and a protrusion provided on the surface of the second substrate. In this case, preferably the protrusion provided on the surface of the first substrate and the protrusion provided on the surface of the second substrate have respective surfaces forming the communication gate that are parallel to or substantially parallel to each other. Further, preferably an angle between the surface of the first substrate forming the first region, and a side surface, abutting on the first region, of the protrusion provided on the surface of the first substrate, is an obtuse angle, and an angle between the surface of the second substrate forming the first region, and a side surface, abutting on the first region, of the protrusion provided on the surface of the second substrate, is an obtuse angle.

Furthermore, the present invention is a microchip including: a first substrate and a second substrate, the first substrate being superposed on the second substrate and having a surface with a groove; and a fluid circuit composed of a cavity defined by the groove and a surface on the first substrate side of the second substrate. The fluid circuit includes a fluid retaining reservoir for containing a fluid. The fluid retaining reservoir includes: a fluid outlet for allowing the fluid to flow out; and at least one columnar body extending in thickness direction of the microchip. The columnar body is provided in a fluid retaining region for retaining the fluid. The fluid retaining region includes a position farthest from the fluid outlet.

Preferably the fluid retaining reservoir includes at least three columnar bodies, and the columnar bodies are disposed at respective positions corresponding to vertexes of a substantially regular triangle. In this case, preferably the columnar bodies are disposed in such a manner that one side of the substantially regular triangle is 0.5 to 1 mm.

Further, preferably the fluid retaining reservoir includes at least two columnar bodies, and the columnar bodies are arranged on a surface of the fluid formed when the whole amount of the fluid contained in the fluid retaining reservoir is retained in the fluid retaining region.

Preferably, the length of the columnar body in the thickness direction of the microchip is substantially identical to the depth of the groove forming the fluid retaining reservoir.

Preferably, the first substrate includes a fluid inlet for injecting the fluid into the fluid retaining reservoir, the fluid inlet is a through opening extending through the first substrate from a surface opposite to the surface with the groove of the first substrate to the fluid retaining reservoir, and at least two columnar bodies are arranged substantially perpendicularly to a line connecting the fluid outlet and the center of the fluid inlet.

Further, the present invention provides a substrate that is the above-described first substrate where the columnar body is disposed in the groove forming the fluid retaining reservoir, and a substrate that is the above-described second substrate where the columnar body is disposed in the groove forming the fluid retaining reservoir.

According to the microchip of the present invention, even if an external impact is applied or the internal pressure of the fluid retaining reservoir increases due to variation of the environmental temperature for example, the fluid (such as liquid reagent) contained in the reservoir can be effectively prevented from flowing out from the fluid retaining reservoir. Further, since the fluid retaining reservoir in the microchip of the present invention can retain the fluid in a state relatively close to a sealed state, an excellent ability to prevent degradation of the fluid is achieved. Furthermore, since the fluid retaining reservoir has a relatively simplified structure, the reservoir is easy to manufacture and problems such as operational malfunction are unlikely to occur.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

First Embodiment

Figure 1:
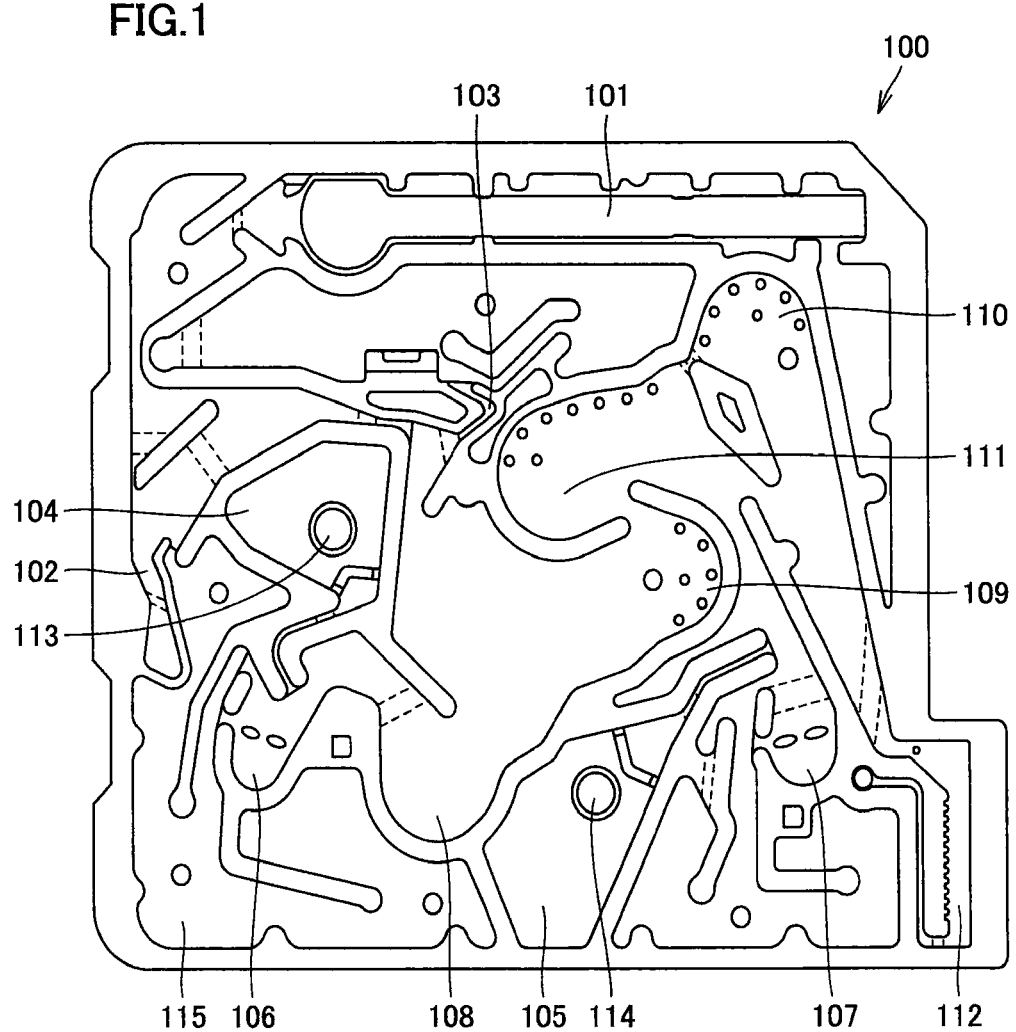
FIG. 1 is a plan view showing a preferred example of a first substrate having a groove in a surface, and used for a microchip according to a first embodiment of the present invention.

A microchip in the present embodiment is a chip with which various types of chemical synthesis, test and analysis for example can be performed by means of a fluid circuit of the microchip. The microchip of the present embodiment in a preferred form is constituted of a second substrate and a first substrate superposed on and bonded onto the second substrate. More specifically, the first substrate having a groove in its surface is bonded onto the second substrate in such a manner that the groove-formed surface of the first substrate is opposite to the second substrate. Thus, the microchip formed of these two substrates includes therein a fluid circuit composed of a cavity defined by the groove provided in the surface of the first substrate and one of the surfaces of the second substrate that is opposite to the first substrate. While the shape and pattern of the groove formed in the surface of the first substrate are not particularly limited to specific ones, the shape and pattern of the groove are determined so that the structure of the cavity made by the groove and the surface of the second substrate is a desired appropriate fluid circuit structure. The first-substrate-side surface of the second substrate may have a groove as well with which a fluid circuit can be formed.

The microchip of the present embodiment in another preferred form is constituted of a first substrate having grooves respectively provided in opposite surfaces of the first substrate, and second and third substrates superposed and bonded in such a manner that the first substrate is sandwiched between the second and third substrates. The microchip constituted of these three substrates includes two layers of fluid circuits, namely a first fluid circuit composed of a cavity defined by one of the surfaces of the second substrate that is opposite to the first substrate and the groove formed in the surface of the first substrate that is opposite to the second substrate, and a second fluid circuit composed of a cavity defined by one of the surfaces of the third substrate that is opposite to the first substrate and the groove formed in the surface of the first substrate that is opposite to the third substrate. Here, "two layers" means that the fluid circuits are provided respectively at two positions that are different in the thickness direction of the microchip. The first fluid circuit and the second fluid circuit may be connected by one through opening or two or more through openings extending through the first substrate in the thickness direction. Further, in the first-substrate-side surfaces/surface of the second substrate and/or the third substrate as well, grooves/groove may be formed with which a fluid circuit can be formed.

The method for bonding the substrates together is not particularly limited to a specific one, and includes those methods such as a method for welding the substrates together by melting a to-be-bonded surface of at least one of the substrates to be bonded to each other (welding method), and a method for joining the substrates together by means of an adhesive, for example. The welding method includes those methods such as a method for welding the substrates together by heating the substrates, a method for welding the substrates together by means of heat generated when the light such as a laser is absorbed, and a method for welding the substrates together by means of ultrasonic waves.

The size of the microchip in the present embodiment is not particularly limited to a specific one, and may be approximately several centimeters in length and width each and approximately several millimeters to one centimeter in thickness.

The material for each of the substrates constituting the microchip in the present embodiment is not particularly limited to a specific one, and may be for example any of organic materials such as polyethylene terephthalate (PET), polybutylene terephthalate (PBT), polymethylmethacrylate (PMMA), polycarbonate (PC), polystyrene (PS), polypropylene (PP), polyethylene (PE), polyethylene naphthalate (PEN), polyarylate resin (PAR), acrylonitrile-butadiene-styrene (ABS) resin, polyvinyl chloride (PVC) resin, polymethylpentene (PMP) resin, polybutadiene (PBD) resin, biodegradable polymer (BP), cycloolefin polymer (COP), and polydimethylsiloxane (PDMS), and inorganic materials such as silicon, glass and quartz.

In the case where the microchip is constituted of two substrates: first substrate and second substrate, the first substrate having a groove in its surface and superposed on the second substrate is not particularly limited to a specific one, and may be for example a transparent substrate. Thus, as a part of the fluid circuit, a detecting portion made by the groove of the transparent first substrate and the surface of the second substrate can be formed. In the microchip having such a detecting portion, a subject to be measured (such as a liquid mixture of a sample to be tested and analyzed and a liquid reagent for example) is introduced into the detecting portion, light is applied to the detecting portion and the intensity (transmittance) of the transmitted light is detected. Thus, the microchip can be used to perform the optical measurement as described above for such a liquid mixture. The second substrate may be a transparent substrate or a colored substrate such as black substrate made of a resin to which carbon black for example is added. The second substrate is preferably a colored substrate, and more preferably a black substrate. A colored substrate can be used as the second substrate so that the welding method by means of light such as a laser can be used. In the case where substrates are bonded together using the laser welding method, the bonding surface of the colored substrate is chiefly melt to be bonded. Therefore, deformation of the groove formed in the transparent substrate that is the first substrate can be kept minimum.

In the case where the microchip is constituted of three substrates: first substrate, second substrate and third substrate, the second substrate and the third substrate holding therebetween the first substrate with respective grooves in the opposite surfaces are not particularly limited to specific ones, and may be transparent substrates. Thus, as a part of the fluid circuit, a detecting portion formed by a through opening extending through the first substrate in the thickness direction of the substrate and respective surfaces of the transparent second and third substrates can be formed. In the microchip having such a detecting portion, a subject to be measured (such as a liquid mixture of a sample to be tested and analyzed and a liquid reagent for example) is introduced into the detecting portion, light in the direction perpendicular to the microchip surface is applied from the upper surface (or lower surface) side of the microchip to the detecting portion, and the intensity (transmittance) of the transmitted light is detected on the opposite side to the light incident side. Thus, the microchip can be used to perform the optical measurement as described above for such a liquid mixture. The first substrate located between the second substrate and the third substrate is preferably a colored substrate and more preferably a black substrate.

The method for forming a groove (flow channel pattern) by which the fluid circuit is made not particularly limited to a specific one, and examples of the method include injection molding method using a mold having a transfer structure and imprinting method for example. In the case where an inorganic material is used to form the substrate, etching may be used for example.

In the microchip of the present embodiment, the fluid circuit (a first fluid circuit and a second fluid circuit where fluid circuits of two layers are included) includes various portions disposed at appropriate positions in the fluid circuit so that various appropriate treatments can be performed on the fluid (such as liquid) in the fluid circuit, and these portions are appropriately connected via a fine flow channel.

In the microchip of the present embodiment, the fluid circuit of the microchip includes, as one of the components of the fluid circuit, a liquid reagent retaining portion serving as a fluid retaining reservoir that is a portion for retaining a liquid reagent which is a fluid. Only one fluid retaining reservoir (such as liquid reagent retaining portion) or two or more fluid retaining reservoirs may be provided in the fluid circuit. "Fluid" refers to a substance with fluidity such as liquid for example. "Liquid reagent" refers to a liquid substance to be mixed or reacted with a sample to be tested and analyzed. One type of liquid reagent or two or more types of liquid reagents may be contained within one microchip. "Sample" refers to a substance (such as blood) itself introduced into the fluid circuit for undergoing a test and an analysis, or a specific component (such as blood plasma component) in the substance.

In the case where the microchip of the present embodiment is constituted of two substrates (first substrate and second substrate), the microchip of the present embodiment is provided with a liquid reagent inlet for injecting a liquid reagent into the liquid reagent retaining portion. The liquid reagent inlet serves as a fluid inlet that is a through opening formed in the upper side surface (namely the surface of the first substrate) and extending through to the inside liquid reagent retaining portion (extending through the first substrate in the direction of the thickness of the first substrate). In such a microchip, usually a liquid reagent which is a fluid is injected from the liquid reagent inlet and thereafter a label or seal is adhered to the surface of the microchip (surface of the first substrate) for sealing the liquid reagent inlet, and accordingly the microchip is provided for use. In the case where the microchip is constituted of three substrates (second substrate/first substrate/third substrate), a liquid reagent inlet may be provided as a through opening extending from the upper side surface of the microchip (the surface of the second or third substrate) to the inside liquid reagent retaining portion (extending through the second or third substrate in the direction of the thickness thereof).

In the microchip of the present embodiment, the fluid circuit may include any component other than the fluid retaining reservoir (liquid reagent retaining portion). Examples of such a component include a separating portion for extracting a specific component from a sample introduced into the fluid circuit, a sample measuring portion for measuring a sample (or a specific component in the sample, the same is applied as well to the following description), a fluid measuring portion (liquid reagent measuring portion) for measuring a fluid such as liquid reagent, a mixing portion for mixing a sample with a fluid such as liquid reagent, and a detecting portion (such as cuvette for performing optical measurement) for testing and analyzing the resultant liquid mixture (detecting or quantitating a specific component in the liquid mixture) for example. The microchip of the present embodiment may include all the above-illustrated components or may not include or one or more of these components. The microchip may include any component other than the above-illustrated components. These components are disposed at appropriate positions in the fluid circuit and connected via a fine flow channel, so that a desired fluid treatment can be performed.

The liquid mixture finally obtained by mixing a sample with a fluid such as liquid reagent is provided for taking an optical measurement, for example, detecting the intensity (transmittance) of the light applied to and transmitted through the component (detecting portion for example) containing the liquid mixture, and the liquid mixture is accordingly tested and analyzed.

Various fluid treatments to be performed in the fluid circuit, such as extraction of a specific component (separation of an unnecessary component) from a sample, measurement of a sample and/or a fluid, mixture of a sample with a fluid, and introduction of the resultant liquid mixture into the detecting portion, for example, can be carried out by successively applying a centrifugal force in an appropriate direction to the microchip. The centrifugal force can be applied to the microchip mounted on an apparatus (centrifugal apparatus) capable of applying a centrifugal force. The centrifugal apparatus includes a freely rotatable rotor (rotating body) and a freely rotatable stage placed on the rotor. The microchip is mounted on the stage and the stage is rotated to set the angle of the microchip with respect to the rotor to an arbitrary angle, so that the centrifugal force in an arbitrary direction can be applied to the microchip.

FIG. 1 is a plan view showing a preferred example of a first substrate 100 having a groove formed in a surface and used for the microchip of the present embodiment, and showing the groove-formed side of first substrate 100. The microchip of the present embodiment is formed by bonding first substrate 100 onto a second substrate (not shown) identical or similar in outline form to first substrate 100, in such a manner that the groove-formed surface of first substrate 100 is located opposite to the second substrate. First substrate 100 and the second substrate are respectively a plastic transparent substrate and a plastic black substrate, for example.

Referring to FIG. 1, the microchip of the present embodiment is chiefly constituted of a sample tube mount portion 101 for incorporating a sample tube such as capillary containing the whole blood taken from a subject, a blood plasma separating portion 102 for removing blood cells for example from the whole blood drawn from the sample tube to obtain a blood plasma component, a sample measuring portion 103 for measuring the separated blood plasma component, two liquid reagent retaining portions 104, 105 serving as fluid retaining reservoirs for retaining a liquid reagent, two liquid reagent measuring portions 106, 107 for measuring the liquid reagent, mixing portions 108, 109, 110, 111 for mixing the blood plasma component with the liquid reagent, and a detecting portion 112 for performing a test and an analysis of the resultant liquid mixture. Two liquid reagent retaining portions 104, 105 have respective liquid reagent inlets 113, 114 for injecting the liquid reagent. Liquid reagent inlets 113, 114 are each a through opening extending through first substrate 100 in the direction of the thickness of the first substrate.

Figure 2:
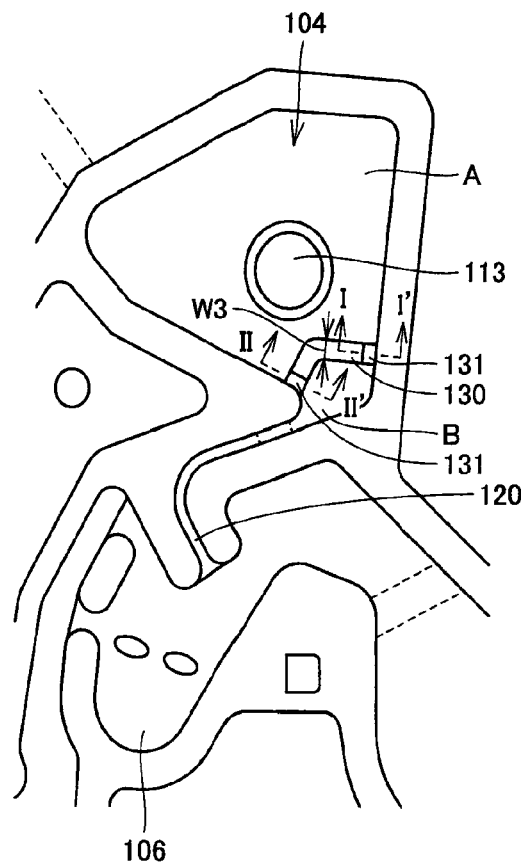
FIG. 2 is an enlarged plan view of a liquid reagent retaining portion of the first substrate shown in FIG. 1.

FIG. 2 is an enlarged plan view of liquid reagent retaining portion 104 of first substrate 100 shown in FIG. 1. As shown in FIG. 2, liquid reagent retaining portion 104 includes an outflow channel 120 for allowing the liquid reagent contained in the retaining portion to flow out. The end opening of outflow channel 120 is located above liquid reagent measuring portion 106. Thus, as a centrifugal force in the downward direction with respect to FIG. 2 (or a centrifugal force in the direction which includes the downward direction with respect to FIG. 2) is applied, for example, the liquid reagent in liquid reagent retaining portion 104 is discharged from the end opening of outflow channel 120 and introduced into liquid reagent measuring portion 106 so that the reagent is measured.

In liquid reagent retaining portion 104, a partition 130 is provided for dividing liquid reagent retaining portion 104 into two sections: a first region A including liquid reagent inlet 113 and a second region B including outflow channel 120. Partition 130 includes two communication gates 131 respectively located at the two opposing ends of partition 130 for allowing communication between first region A and second region B. Partition 130 has a V-shaped cross section in the direction parallel to the surface of first substrate 100 (the surface having the groove) shown in FIG. 2. A similar partition is provided in liquid reagent retaining portion 105 as well, which will not be described in detail (see FIG. 1).

When a liquid reagent is injected into liquid reagent retaining portion 104 of the microchip in the present embodiment structured in the above-described manner, the liquid reagent injected from liquid reagent inlet 113 to be contained in first region A is less likely to flow out into second region B even if an impact is exerted on the microchip, since two communication gates 131 function as a valve. Namely, the liquid reagent retaining portion of the microchip in the present embodiment has a superior function of retaining the liquid reagent against impact, and thus can effectively suppress or prevent unintended outflow of the liquid reagent from the liquid reagent retaining portion due to impact. The function of the valve here refers to the function that undesired discharge of the liquid reagent is prevented while desired discharge can be done by application of a centrifugal force with a predetermined strength. In the present embodiment, outflow channel 120 also has the valve function. Therefore, liquid reagent retaining portion 104 has the two-stage valve function. Since outflow channel 120 has the valve function, even if any impact causes the liquid reagent to flow out from communication gate 131 into second region B, the possibility that the liquid reagent flows out of liquid reagent retaining portion 104 can be made extremely low.

Further, as partition 130 is disposed, the liquid reagent being injected into liquid reagent retaining portion 104 can be suppressed or prevented from closing the inside opening (opening relatively closer to first region A) of outflow channel 120. Further, the reagent can be prevented from moving to close the inside opening of outflow channel 120 due to impact as described above. Therefore, outflow, from the liquid reagent retaining portion, of the liquid reagent closing the inside opening can be suppressed or prevented that is caused by an increase of the internal pressure in the liquid reagent retaining portion due to an increase of the environmental temperature.

Figure 3:
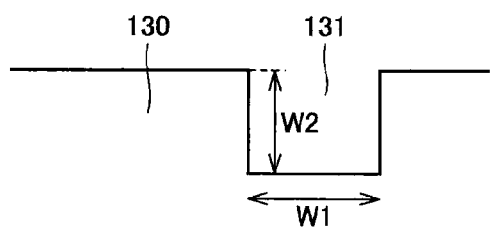
FIG. 3 is a schematic cross-sectional view of a partition along line I-I' shown in FIG. 2.

FIG. 3 is a schematic cross-sectional view of partition 130 along line I-I' shown in FIG. 2. As shown in FIG. 3, communication gate 131 may have a square or rectangular cross section. In order to allow communication gate 131 to have the valve function, width W1 and height W2 of communication gate 131 are each preferably 0.1 to 0.4 mm, and more preferably 0.2 to 0.3 mm. If two or more communication gates are provided like the example shown in FIG. 2, respective cross-sectional shapes of the communication gates may be identical to or different from each other. Further, the cross-sectional shape of the communication gate may be identical or may vary along the whole dimension in the direction of length (direction of the length refers to the direction of thickness W3 of partition 130 shown in FIG. 2). Specifically, in the former case (the cross-sectional shape of communication gate 131 is identical along the whole dimension in the direction of thickness W3), the cross sectional shape of communication gate 131 at the end abutting on first region A, the cross sectional shape thereof at the other end abutting on second region B and the cross-sectional shape thereof between these ends are all identical or substantially identical to each other. The communication gate having the above-described shape is preferable because such a communication gate is relatively easy to process.

Figure 4:
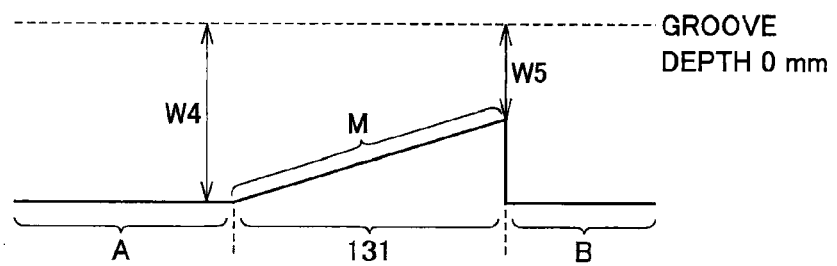
FIG. 4 is a schematic diagram showing an example of a cross section of the partition along line II-II' shown in FIG. 2.

In the case where the cross-sectional shape of the communication gate varies in the direction of length (thickness W3), (i) height W2 of the communication gate is constant while width W1 continuously decreases or increases, or (ii) width W1 of the communication gate is constant while height W2 continuously decreases or increases, for example. A more specific example of case (ii) above is shown in FIG. 4. FIG. 4 is a schematic diagram showing an example of the cross section of partition 130 along line II-II' shown in FIG. 2. In this example as shown in FIG. 4, on the groove-formed surface of first substrate 100, the bottom of the groove that constitutes a part of the inner wall of communication gate 131 becomes gradually shallower from first region A toward second region B to form an inclined surface M. Inclined surface M is the surface forming the upper inner wall of the communication gate when first substrate 100 is superposed on the second substrate (namely it is supposed here that the first substrate is located on the "upper side" with respect to the second substrate). Therefore, in the microchip using first substrate 100 having the structure shown in FIG. 4, the upper inner wall surface of the communication gate inclines in such a manner that height W2 of the communication gate decreases from the first region A side toward the second region B side. Thus, the first substrate surface forming the upper inner wall surface of the communication gate is gradually inclined in such a manner that the groove depth is initially identical to that of first region A and then gradually decreases, and accordingly the liquid reagent can be successfully flown from the first region A side toward the second region B side without leaving liquid.

In the case where the microchip is structured using the first substrate having the groove shape as shown in FIG. 4, depth W4 of the groove forming first region A may be approximately 1.0 to 5.0 mm and preferably approximately 1.5 to 2.5 mm, for example. Groove depth W5 of inclined surface M at the end abutting on the second region may be approximately 0.1 to 0.4 mm and preferably approximately 0.2 to 0.3 mm, for example.

In the example shown in FIG. 2, partition 130 has two communication gates 131, and these communication gates are disposed at the two opposing ends of partition 130, respectively. In the case where the portion of the liquid reagent located in the region opposite to partition 130 with respect to liquid reagent inlet 113 in first region A is to be caused to flow through the communication gates into second region B by applying a centrifugal force, the liquid reagent is more likely to flow along the sidewall surface of first region A to reach partition 130 because of the influence of the surface tension of the liquid reagent. Therefore, the communication gates may be disposed at the two opposing ends of the partition, namely along the sidewall surface of the liquid reagent retaining portion, so that the liquid reagent can be successfully discharged. Further, the cross section of partition 130 in the direction parallel to the surface (groove-formed surface) of first substrate 100 has a V-shape protruding toward first region A. The partition having such a shape can be used to guide the liquid reagent having reached any portion other than the portions where communication gates 131 of partition 130 are formed, toward communication gates 131. Thus, the liquid reagent can be prevented from remaining around partition 130. The cross-sectional shape of partition 130 is not limited to the V shape, and may be the U shape protruding toward first region A. A part of partition 130 may have such a V or U shape.

Thickness W3 of partition 130 is not particularly limited to a specific one, and may be approximately 0.5 to 1.5 mm, and preferably approximately 0.5 to 1.0 mm, for example. Thickness W3 of partition 130 may not necessarily be constant.

The position of partition 130 in liquid reagent retaining portion 104 is not particularly limited to a specific one, as long as the partition is disposed between liquid reagent inlet 113 and the inside opening (opening abutting on first region A) of outflow channel 120. In terms of securing a space for temporarily accommodating the liquid reagent flowing out from communication gate 131 and for preventing the liquid reagent from occupying outflow channel 120, it is preferable that second region B between partition 130 and outflow channel 120 has an adequate volume.

Outflow channel 120 may have a square or rectangular cross section like communication gate 131. In order to allow outflow channel 120 to have the valve function, preferably the width and height of outflow channel 120 are each 0.1 to 0.4 mm, and more preferably 0.2 to 0.3 mm. The cross-sectional shape of the outflow channel may be identical or may vary along the whole dimension in the direction of length. Further, outflow channel 120 and communication gate 131 may be identical to or different from each other in width and height.

The microchip of the present embodiment may be modified in various manners in addition to the above-described ones as long as the modifications fall within what is intended by the present invention. The modifications may include the following ones.

Figure 5:
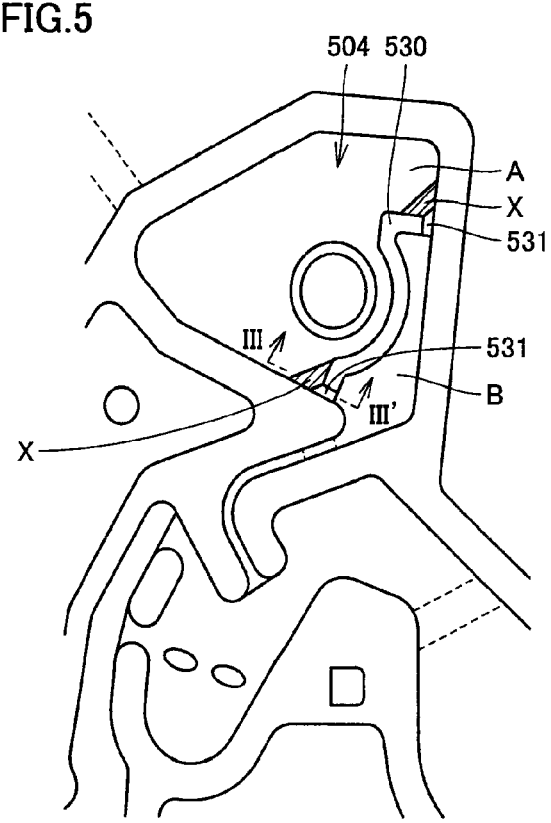
FIG. 5 is an enlarged plan view showing another preferred example of the liquid reagent retaining portion according to the first embodiment of the present invention.

(1) Like a liquid reagent retaining portion 504 shown in FIG. 5, a partition 530 may have a cross section parallel to the surface (groove-formed surface) of the first substrate that is a V or U shape protruding toward second region B. Any appropriate cross-sectional shape like the above-described one may be selected for the purpose of providing the partition within the limited space.

Figure 6:
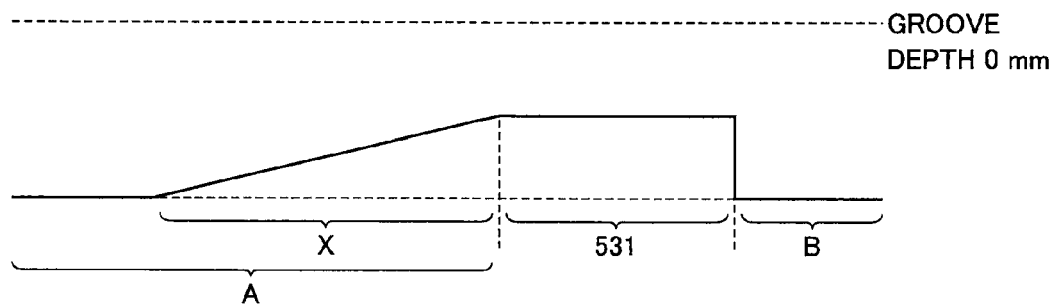
FIG. 6 is a schematic cross-sectional view of a partition and its peripheral portion along line III-III' shown in FIG. 5.

(2) As shown in FIG. 5 and FIG. 6 (schematic cross-sectional view of a partition and its peripheral portion along line III-III' shown in FIG. 5), on the bottom of the groove of the first substrate that forms the upper inner wall surface of first region A, the depth of the groove section in region X adjacent to a communication gate 531 may become shallower toward communication gate 531. In the microchip using the first substrate having the above-described incline structure, the upper inner wall surface of first region A includes the portion in region X of the liquid reagent retaining portion where the height decreases toward communication gate 531. Thus, the bottom of the groove in region X is inclined in such a manner that the depth which is initially identical to that of first region A other than region X gradually decreases, so that the liquid reagent can be successfully flown out from first region A into second region B without leaving the liquid. In the case where region X has the inclined structure, the bottom of the groove forming the upper inner wall surface of the communication gate may not necessarily have the inclined structure.

(3) The number of the communication gates is not limited to two, and one communication gate may be provided. As long as one communication gate having the valve function is provided, the liquid reagent retaining ability can be improved. It should be noted, however, that two communication gates are preferably provided in order to prevent the liquid reagent from being moved due to impact to occupy all of the communication gates. Three or more communication gates may be provided.

The liquid reagent retaining portion may not necessarily have the outflow channel, and may include only a liquid reagent outlet for allowing the liquid reagent to flow out. In terms of further preventing the liquid reagent retaining ability, however, it is preferable to provide the outflow channel.

An operational method of the microchip in the present embodiment using the first substrate shown in FIGS. 1 and 2 will be generally described. Here, the operational method described below is an exemplary one, and is not limited to the method as described. First, a sample tube into which a sample of the whole blood is taken is inserted into sample tube mount portion 101. Next, a centrifugal force in the leftward direction with respect to FIG. 1 (hereinafter simply referred to as leftward centrifugal force, centrifugal forces in other directions will be called similarly below) is applied to the microchip to draw out the whole-blood sample in the sample tube. After this, a downward centrifugal force is applied to cause the whole-blood sample to be introduced into plasma separating portion 102 where the blood is separated into a blood plasma component and a blood cell component by centrifugal separation. When the whole-blood sample is introduced into plasma separating portion 102, an overflowing whole-blood sample portion is received in a waste liquid storage 115. The downward centrifugal force also causes a liquid reagent S1 retained in first region A of liquid reagent retaining portion 104 to flow out into second region B through communication gates 131 and further flow through outflow channel 120 to be introduced into a liquid reagent measuring portion 106 where the liquid reagent is measured.

Subsequently, the separated blood plasma component is introduced into a sample measuring portion 103 by a rightward centrifugal force. At this time, the measured liquid reagent S1 is moved to mixing portion 109, and a liquid reagent S2 in liquid reagent retaining portion 105 is discharged through the communication gates from the outflow channel.

Next, a downward centrifugal force is applied. Accordingly, the measured blood plasma component and the measured liquid reagent S1 are mixed in mixing portion 108, and liquid reagent S2 is measured by liquid reagent measuring portion 107. Then, rightward, downward and rightward centrifugal forces are applied successively to move the liquid mixture between mixture portions 108 and 109 so that the liquid mixture is sufficiently mixed.

Next, an upward centrifugal force is applied. Accordingly, the liquid mixture of liquid reagent S1 and the blood plasma component is mixed with the measured liquid reagent S2 in a mixing portion 110. Then, leftward, upward, leftward, and upward centrifugal forces are successively applied to move the liquid mixture between mixing portions 110 and 111 so that the liquid mixture is sufficiently mixed.

Finally, a rightward centrifugal force is applied to introduce the liquid mixture in mixing portion 110 into detecting portion 112. The liquid mixture in detecting portion 112 undergoes optical measurement by means of light applied to detecting portion 112. For example, the intensity of the transmitted light is measured.

Second Embodiment

A microchip of the present embodiment will be described in connection with a preferred example thereof While characteristic features of the microchip of the present embodiment will be chiefly described below, other features are similar to those of the first embodiment as described above.

Figure 7:
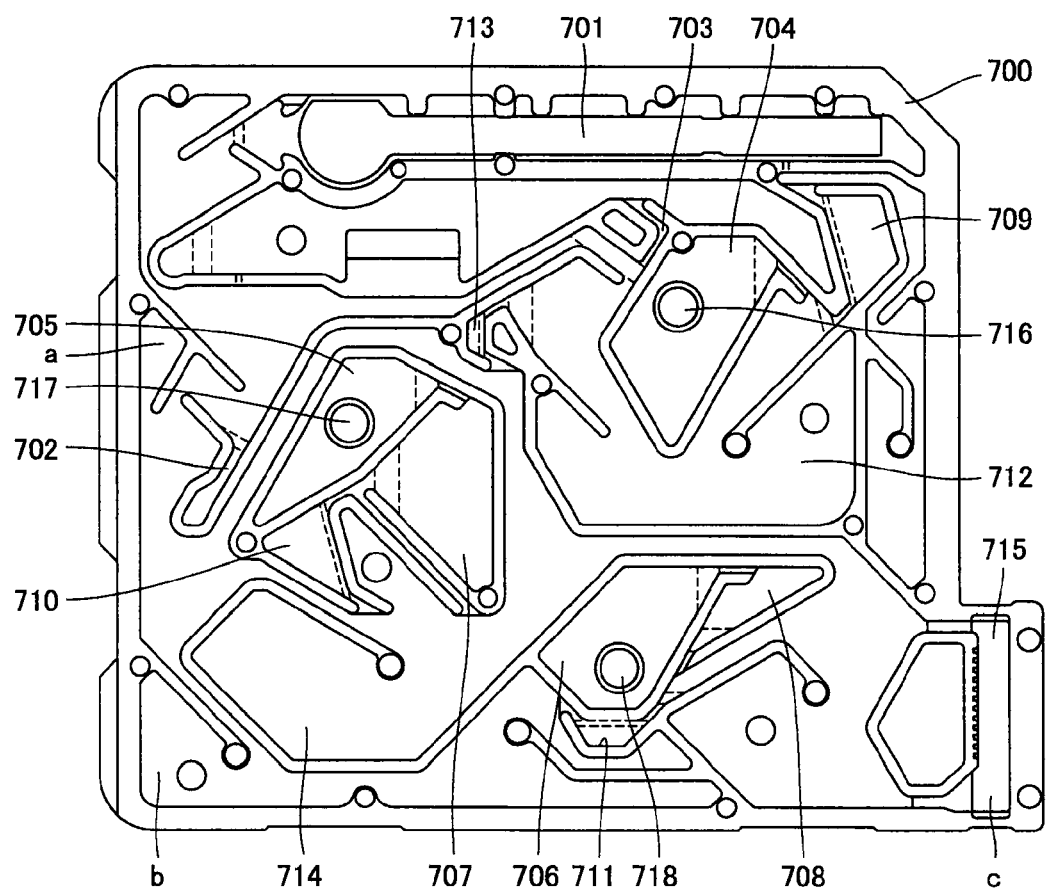
FIG. 7 is a top view showing a preferred example of a microchip according to a second embodiment of the present invention, formed by superposing and bonding a first substrate having a groove in a surface onto a second substrate.

FIG. 7 is a top view showing a preferred example of the microchip of the present embodiment, formed by superposing and bonding a first substrate 700 having a groove in a surface on a second substrate (not shown). In the microchip shown in FIG. 7, first substrate 700 is bonded to the second substrate (not shown) in such a manner that the groove-formed surface of the first substrate is located opposite to the second substrate. While FIG. 7 shows the surface of first substrate 700 that is opposite to the groove-formed surface thereof, a groove pattern is indicated by the solid line for convenience of description. In the microchip shown in FIG. 7, the second substrate is identical or similar in outline form to first substrate 700. First substrate 700 and the second substrate are respectively a plastic transparent substrate and a plastic black substrate, for example.

The microchip shown in FIG. 7 is chiefly constituted of a sample tube mount portion 701 for incorporating a sample tube such as capillary containing the whole blood taken from a subject, a separating portion 702 for separating the whole blood drawn from the sample tube into a blood cell component and a blood plasma component, a blood cell measuring portion 703 for measuring the separated blood cell component, three liquid reagent retaining portions 704, 705 and 706 serving as fluid retaining reservoirs for retaining a liquid reagent, liquid reagent containers 707 and 708 serving as fluid containing reservoirs provided adjacent to liquid reagent retaining portions 705 and 706 respectively for temporarily containing the liquid reagent, three liquid reagent measuring portions 709, 710 and 711 for measuring the liquid reagent, a first mixing portion 712 for mixing the blood cell component with the liquid reagent, a liquid mixture measuring portion 713 for measuring the liquid mixture of the blood cell component and the liquid reagent, a second mixing portion 714 for mixing the liquid mixture of the blood cell component and the liquid reagent with another liquid reagent, and a detecting portion 715 where a test and an analysis are conducted for the finally obtained liquid mixture. The three liquid reagent retaining portions 704, 705 and 706 respectively include liquid reagent inlets 716, 717 and 718 for injecting the liquid reagent into the corresponding liquid reagent retaining portions. Liquid reagent inlets 716, 717 and 718 that are fluid inlets are through openings extending through first substrate 700 in the thickness direction. In the following, respective liquid reagents injected via the liquid reagent inlets and retained in respective liquid reagent retaining portions 704, 705 and 706 will be referred to as liquid reagents R0, R1 and R2 respectively.

As seen from above, the fluid circuit of the microchip shown in FIG. 7 has a structure appropriate for mixing the blood cell component separated from the whole blood with liquid reagents R0, R1 and R2 in this order and performing a test and an analysis such as optical measurement on the resultant liquid mixture. In the following, a liquid reagent retaining portion and a peripheral portion thereof that is a characteristic feature of the present embodiment will be described in detail in connection with liquid reagent retaining portion 705 as an example.

Figure 8:
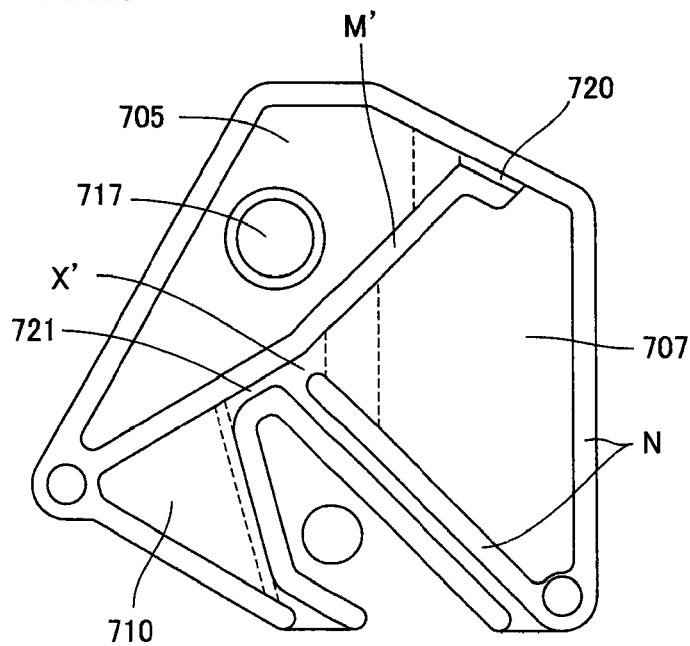
FIG. 8 is an enlarged top view of a liquid reagent retaining portion and its peripheral portion of the microchip shown in FIG. 7.

FIG. 8 is an enlarged top view of liquid reagent retaining portion 705 and its peripheral portion of the microchip shown in FIG. 7. As shown in FIG. 8, in the microchip shown in FIG. 7, liquid reagent container 707 for temporarily containing liquid reagent R1 is provided adjacent to liquid reagent retaining portion 705 retaining liquid reagent R1. Specifically, a first outflow channel 720 is provided for allowing liquid reagent R1 injected from liquid reagent inlet 717 and retained in liquid reagent retaining portion 705 to flow out. One end of first outflow channel 720 is connected to an end of liquid reagent retaining portion 705 and the other end thereof is connected to liquid reagent container 707. Liquid reagent container 707 is disposed to allow liquid reagent R1 flowing out from liquid reagent retaining portion 705 to be temporarily contained in liquid reagent container 707. Liquid reagent container 707 is formed by a region defined by a part of a wall M' forming liquid reagent retaining portion 705 and a wall N located to surround the peripheral portion of first outflow channel 720.

Liquid reagent container 707 has an opening (opening X' in FIG. 8) separately from the opening at the portion connected to first outflow channel 720. To opening X', a second outflow channel 721 is connected for allowing liquid reagent R1 to flow out from liquid reagent container 707. The other end of second outflow channel 721 is directly connected to liquid reagent measuring portion 710. Thus, as a centrifugal force in an appropriate direction is applied (leftward centrifugal force in FIG. 8 for example), liquid reagent R1 is discharged from liquid reagent container 707 and liquid reagent R1 is then introduced into liquid reagent measuring portion 710 by the centrifugal force and measured.

Since liquid reagent container 707 having the above-described structure and capable of temporarily containing liquid reagent R1 flowing out from liquid reagent retaining portion 705 is provided, even if an external impact is exerted on the microchip or the internal pressure of liquid reagent retaining portion 705 increases, for example, liquid reagent R1 can be prevented from flowing out into liquid reagent measuring portion 710. Specifically, first outflow channel 720 is a fine flow channel and itself functions as a valve, and thus outflow from liquid reagent retaining portion 705 into liquid reagent container 707 is relatively less likely to occur in this structure. If, however, the microchip is subjected to an external impact, unintended outflow could occur. For example, there could be the case where liquid reagent R1 is discharged from liquid reagent retaining portion 705 by the impact. There could also be the case where impact causes liquid reagent R1 to move to occupy the opening of first outflow channel 720 and, when a subsequent increase in environmental temperature causes the internal pressure of liquid reagent retaining portion 705 to increase, liquid reagent R1 occupying the opening could be discharged. Even in these cases, liquid reagent container 707 is provided to allow liquid reagent R1 flowing out from liquid reagent retaining portion 705 to be contained in liquid reagent container 707, so that liquid reagent R1 can be prevented from flowing out into liquid reagent measuring portion 710. The function of valve here refers to the function that undesired discharge of the liquid reagent is prevented while desired discharge can be done by application of a centrifugal force with a predetermined strength. Further, since liquid reagent R1 is retained in a nearly sealed state until the microchip is used, quality degradation is less likely to occur.

If the microchip contains a plurality of different types of liquid reagents, the liquid reagent container may serve to temporarily keep the reagent on standby. Accordingly, the liquid reagents can be introduced at appropriate timings respectively into the measuring portions and can be mixed at proper timings respectively with the sample. The microchip having such a liquid reagent container is particularly useful in the case where a plurality of different types of liquid reagents have to be mixed successively in an appropriate order with the sample.

In the microchip shown in FIGS. 7 and 8, second outflow channel 721 connecting liquid reagent container 707 and liquid reagent measuring portion 710 also has the valve function, like first outflow channel 720. Therefore, as a centrifugal force with a predetermined strength is applied, liquid reagent R1 contained in liquid reagent container 707 is introduced into liquid reagent measuring portion 710. Liquid reagent retaining portion 705 may not necessarily have first outflow channel 720. Instead of the outflow channel, an opening such as through opening extending through wall M' which forms liquid reagent retaining portion 705 may be provided to connect liquid reagent retaining portion 705 and liquid reagent container 707 by the opening. Likewise, liquid reagent container 707 may not necessarily have second outflow channel 720. Instead, an opening such as through opening extending through wall N which forms liquid reagent container 707 may be provided to connect liquid reagent container 707 and liquid reagent measuring portion 710 by the opening. It should be noted, however, that preferably these portions are connected by the outflow channels for allowing the valve function to successfully work. In order to effect a favorable valve function, the width of first outflow channel 720 and second outflow channel 721 is preferably approximately 0.1 to 0.5 mm and more preferably approximately 0.3 mm. The length of first outflow channel 720 and second outflow channel 721 is preferably approximately 0.6 to 3.0 mm and more preferably approximately 1.2 to 2.0 mm.

Second outflow channel 721 preferably extends in a direction different from first outflow channel 720 as shown in FIG. 8. More preferably, first outflow channel 720 and second outflow channel 721 are disposed in such a manner that the direction of the flow of liquid reagent R1 in first outflow channel 720 and that of liquid reagent R1 in second outflow channel 721 make an angle of 90° to 180°. Accordingly, in the case where liquid reagent container 707 has the function of keeping the liquid reagent on standby as described above, liquid reagent R1 can be prevented from flowing directly into liquid reagent measuring portion 710 without being contained in liquid regent container 707, by the same centrifugal force as the centrifugal force for moving liquid reagent R1 from liquid reagent retaining portion 705 to liquid reagent container 707.

Second outflow channel 721 and opening X' to which second outflow channel 721 is connected are preferably disposed at the wall forming liquid reagent container 707, at a position relatively closer to liquid reagent retaining portion 705. More preferably, second outflow channel 721 and opening X are provided along wall M' forming liquid reagent retaining portion 705. Thus, the liquid reagent retaining portion and its peripheral portion can be more integrated.

Figure 9:
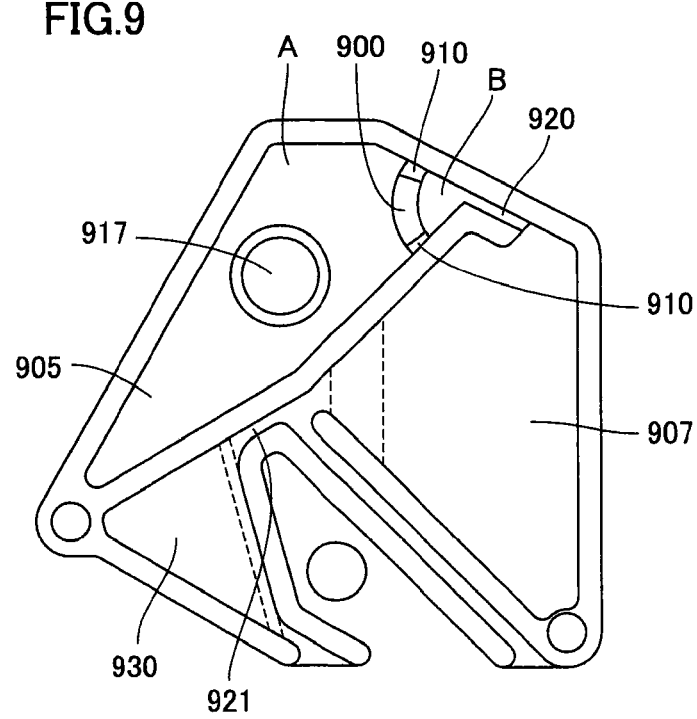
FIG. 9 is an enlarged top view of a liquid reagent retaining portion and its peripheral portion in another preferred example of the microchip according to the second embodiment of the present invention.

In the present embodiment, a partition may be provided in the liquid reagent retaining portion for dividing the liquid reagent retaining portion into two sections. FIG. 9 is an enlarged top view of a liquid reagent retaining portion and its peripheral portion in another preferred example of the microchip in the present embodiment. In a liquid reagent retaining portion 905 shown in FIG. 9, a partition 900 is provided that divides liquid reagent retaining portion 905 into a first region A including a liquid reagent inlet 917 and a second region B including a first outflow channel 920. Partition 900 has two communication gates 910 at the two opposing ends of partition 900 respectively, for allowing communication between first region A and second region B. A cross section of partition 900 in the direction parallel to the groove-formed surface of the first substrate is in the U-shape protruding toward first region A.

Here, a liquid reagent container 907 for temporarily containing the liquid reagent is provided adjacent to liquid reagent retaining portion 905. Liquid reagent container 907 is connected to a second outflow channel 921 for allowing the liquid reagent to flow out. The other end of second outflow channel 921 is connected to a liquid reagent measuring portion 930. These components are similar to those shown in FIG. 8.

Partition 900 having such communication gates 910 is thus provided in liquid reagent retaining portion 905. Then, when liquid reagent R1 is injected into liquid reagent retaining portion 905, liquid reagent R1 injected from liquid reagent inlet 917 and contained in first region A is less likely to flow out into second region B even if impact is exerted on the microchip, since two communication gates 910 function as valves. Namely, the liquid reagent retaining portion including such a partition has a further superior ability to retain the liquid reagent against impact, and unintended outflow of the liquid reagent from the liquid reagent retaining portion due to impact can be more effectively suppressed or prevented.

Since partition 910 is disposed, liquid reagent R1 when injected into liquid reagent retaining portion 905 can be suppressed or prevented from occupying the inside opening of first outflow channel 920 (the opening abutting on liquid reagent retaining portion 905). Further, it can be suppressed or prevented that the liquid reagent is caused to move due to impact to occupy the inside opening of first outflow channel 920, and thus liquid reagent R1 occupying the inside opening can be suppressed or prevented from flowing out from liquid reagent retaining portion 905 due to an increase of the internal pressure of liquid reagent retaining portion 905 caused by an increase of the environmental temperature for example.

The cross-sectional shape of communication gate 910 is not particularly limited to a specific one, and may be square or rectangular for example. In order to allow communication gate 910 to have the valve function, the width and the height of communication gate 910 are each preferably 0.1 to 0.5 mm, and more preferably 0.2 to 0.3 mm. If two or more communication gates are provided like the example shown in FIG. 9, respective cross-sectional shapes of the communication gates may be identical to or different from each other. Further, the cross-sectional shape of the communication gate may be identical or may vary along the whole dimension in the direction of the length (direction of the length refers to the direction of the thickness of partition 900 shown in FIG. 9). Specifically, in the former case (the cross-sectional shape of communication gate 910 is identical along the whole dimension in the direction of the thickness), the cross sectional shape of communication gate 910 at the end abutting on first region A, the cross sectional shape thereof at the other end abutting on second region B and the cross-sectional shape thereof between these ends are all identical or substantially identical to each other. The communication gate having the above-described shape is preferable because such a communication gate is relatively easy to process.

In the case where the cross-sectional shape of the communication gate varies in the direction of the length, (i) the height of the communication gate is constant while the width continuously decreases or increases, or (ii) the width of the communication gate is constant while the height continuously decreases or increases, for example. A more specific example of case (ii) above is as follows. On the groove-formed surface of the first substrate, the bottom of the groove that constitutes a part of the inner wall surface of communication gate 910 becomes gradually shallower from first region A toward second region B to form an inclined surface (the inclined surface is the surface forming the upper inner wall surface of the communication gate when the first substrate is superposed on the second substrate (namely it is supposed here that the first substrate is located on the "upper side" with respect to the second substrate)). In this case, the upper inner wall surface of the communication gate inclines in such a manner that the height of the communication gate decreases from the first region A side toward the second region B side. Thus, the first substrate surface forming the upper inner wall surface of the communication gate is gradually inclined in such a manner that the groove depth is initially identical to that of first region A and then gradually decreases, and accordingly the liquid reagent can be successfully flown from the first region A side toward the second region B side without leaving the liquid.

In the example shown in FIG. 9, partition 900 has two communication gates 910, and these communication gates are disposed at the two opposing ends of partition 900, respectively. In the case where the portion of liquid reagent R1 located in the region opposite to partition 900 with respect to liquid reagent inlet 917 in first region A is to be caused to flow through communication gates 910 into second region B by applying a centrifugal force, liquid reagent R1 is more likely to flow along the sidewall surface of first region A to reach partition 900 because of the influence of the surface tension of the liquid reagent. Therefore, the communication gates may be disposed at the two opposing ends of the partition, namely along the sidewall surface of the liquid reagent retaining portion, so that liquid reagent R1 can be successfully discharged.

Further, the cross section of partition 900 in the direction parallel to the groove-formed surface of the first substrate has a U shape protruding toward first region A. The partition having such a shape can be used to guide liquid reagent R1 having reached any portion other than the portions where communication gates 910 of partition 900 are formed, toward communication gates 910. Thus, the liquid reagent can be prevented from remaining around partition 900. The cross-sectional shape of partition 900 is not limited to the U shape, and may be a V shape protruding toward first region A. A part of partition 900 may have such a V or U shape.

The thickness of partition 900 is not particularly limited to a specific one, and may be approximately 0.5 to 1.5 mm, and preferably approximately 0.5 to 1.0 mm, for example. The thickness of partition 900 may not necessarily be constant.

The position of partition 900 in liquid reagent retaining portion 905 is not particularly limited to a specific one, as long as the partition is disposed between liquid reagent inlet 917 and the inside opening of first outflow channel 920. In terms of securing a space for temporarily accommodating liquid reagent R1 flowing out from communication gate 910 and for preventing liquid reagent R1 from occupying first outflow channel 920, it is preferable that second region B between partition 900 and first outflow channel 920 has an adequate volume.

Partition 900 may have a cross section parallel to the groove-formed surface of the first substrate that is a V or U-shape protruding toward second region B. Any appropriate cross-sectional shape like the above-described one may be selected for the purpose of providing the partition within the limited space. The number of the communication gates is not limited to two, and one communication gate may be provided. As long as one communication gate having the valve function is provided, the liquid reagent retaining ability can be improved. It should be noted, however, that two communication gates are preferably provided in order to prevent the liquid reagent from being moved due to impact to occupy all of the communication gates. Three or more communication gates may be provided.

An operational method of the microchip shown in FIG. 7 will be generally described. Here, the operational method described below is an exemplary one, and is not limited to the method as described. First, a sample tube into which a sample of the whole blood is taken is inserted into sample tube mount portion 701. Next, a centrifugal force in the leftward direction with respect to FIG. 7 (hereinafter simply referred to as leftward centrifugal force, centrifugal forces in other directions will be called similarly below) is applied to the microchip to draw out the whole-blood sample in the sample tube. After this, a downward centrifugal force is applied to cause the whole-blood sample to be introduced into separating portion 702 where the blood is separated into a blood plasma component and a blood cell component by centrifugal separation. Next, a leftward centrifugal force is applied to remove the blood plasma component in the upper layer. At this time, the removed blood plasma component is received in a region "a." Subsequently, a downward centrifugal force is applied to smooth the surface of the blood cell component in separating portion 702, and move the removed blood plasma component to a region "b." Next, a rightward centrifugal force is applied to introduce liquid reagent R0 in liquid reagent retaining portion 704 into liquid reagent measuring portion 709 to measure the liquid reagent. This centrifugal force causes liquid reagent R1 in liquid reagent retaining portion 705 and liquid reagent R2 in liquid reagent retaining portion 706 to move to liquid reagent containers 707 and 708 respectively. This centrifugal force also causes the blood cell component in separating portion 702 to be introduced into blood cell measuring portion 703 and measured therein.

Next, a downward centrifugal force is applied to mix the measured blood cell component with liquid reagent R0 in first mixing portion 712 to produce a liquid mixture. This centrifugal force causes liquid reagent R2 in liquid reagent container 708 to be measured in liquid reagent measuring portion 711. Then, rightward, downward, leftward, and downward centrifugal forces are successively applied to sufficiently mix the liquid mixture. This leftward centrifugal force allows liquid reagent R1 in liquid reagent container 707 to be measured by liquid reagent measuring portion 710. Further, the last downward centrifugal force causes the measured liquid reagent R1 to move to second mixing portion 714.

Next, a leftward centrifugal force is applied and thereafter an upper-leftward centrifugal force and then a leftward centrifugal force are applied to introduce the supernatant portion of the liquid mixture in first mixing portion 712 into liquid mixture measuring portion 713 and measured therein. Then, a downward centrifugal force is applied to mix the measured liquid mixture with liquid reagent R1 in second mixing portion 714. Subsequently, leftward and downward centrifugal forces are successively applied to sufficiently mix the liquid mixture. In the state where the downward centrifugal force is applied, the measured liquid reagent R2 is located in a region "c." Next, a rightward centrifugal force is applied to mix the liquid mixture with liquid reagent R2 in detecting portion 715. Further, a downward centrifugal force is applied to sufficiently mix the liquid mixture with the liquid reagent. Finally, a rightward centrifugal force is applied so that the liquid mixture is contained in detecting portion 715. Light is applied to detecting portion 715 and optical measurement is performed such as measurement of the intensity of the transmitted light, for example.

Third Embodiment

A microchip of the present embodiment will be described in connection with some preferred examples thereof While characteristic features of the microchip of the present embodiment will be chiefly described below, other features are similar to those of the first embodiment as described above.

Figure 10:
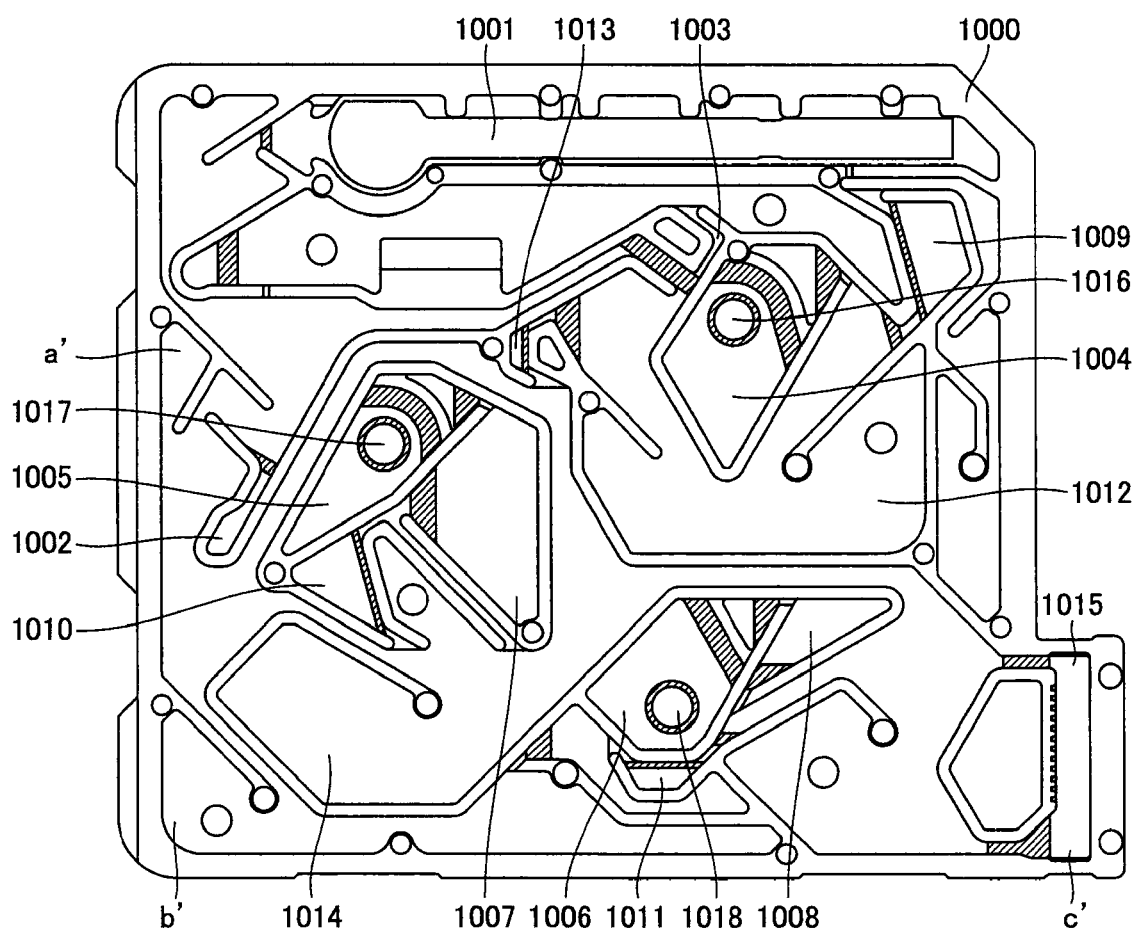
FIG. 10 is a top view showing a preferred example of a microchip according to a third embodiment of the present invention, formed by superposing and bonding a first substrate having a groove formed in a surface onto a second substrate.

FIG. 10 is a top view showing a preferred example of a microchip of the present embodiment, formed by superposing and bonding a first substrate 1000 having a groove formed in a surface onto a second substrate 200 (not shown in FIG. 10) and showing a fluid circuit of the microchip. In the microchip shown in FIG. 10, first substrate 1000 is bonded to second substrate 200 (not shown) in such a manner that the groove-formed surface of the first substrate is located opposite to the second substrate. While FIG. 10 shows the surface of first substrate 1000 that is opposite to the groove-formed surface thereof, a groove pattern is indicated by the solid line for convenience of description. In the microchip shown in FIG. 10, second substrate 200 is identical or similar in outline form to first substrate 1000. First substrate 1000 and second substrate 200 are respectively a plastic transparent substrate and a plastic black substrate, for example. The hatching in some regions of FIG. 10 means that the region indicated by the hatching is tapered (specifically the bottom of the groove in the hatched region is inclined relative to the bottom of the groove in an adjacent region). The same is applied as well to the hatching in FIG. 11 described below.

A fluid circuit of the microchip shown in FIG. 10 is chiefly constituted of a sample tube mount portion 1001 for incorporating a sample tube such as capillary containing the whole blood taken from a subject, a separating portion 1002 for separating the whole blood drawn from the sample tube into a blood cell component and a blood plasma component, a blood cell measuring portion 1003 for measuring the separated blood cell component, three liquid reagent retaining portions 1004, 1005 and 1006 serving as fluid retaining reservoirs for retaining a liquid reagent, liquid reagent containers 1007 and 1008 serving as fluid containing reservoirs provided adjacent to liquid reagent retaining portions 1005 and 1006 respectively for temporarily containing the liquid reagent, three liquid reagent measuring portions 1009, 1010 and 1011 for measuring the liquid reagent, a first mixing portion 1012 for mixing the blood cell component with the liquid reagent, a liquid mixture measuring portion 1013 for measuring the liquid mixture of the blood cell component and the liquid reagent, a second mixing portion 1014 for mixing the liquid mixture of the blood cell component and the liquid reagent with another liquid reagent, and a detecting portion 1015 where a test and an analysis are conducted for the finally obtained liquid mixture. The three liquid reagent retaining portions 1004, 1005 and 1006 respectively include liquid reagent inlets 1016, 1017 and 1018 for injecting the liquid reagent into the corresponding liquid reagent retaining portions. Liquid reagent inlets 1016, 1017 and 1018 that are fluid inlets are through openings extending through first substrate 1000 in the thickness direction. In the following, respective liquid reagents injected via the liquid reagent inlets and retained in respective liquid reagent retaining portions 1004, 1005 and 1006 will be referred to as liquid reagents R0, R1 and R2 respectively.

As seen from above, the fluid circuit of the microchip shown in FIG. 10 has a structure appropriate for mixing the blood cell component separated from the whole blood with liquid reagents R0, R1 and R2 in this order and performing a test and an analysis such as optical measurement on the resultant liquid mixture. In the following, a liquid reagent retaining portion serving as a fluid retaining reservoir that is a characteristic feature of the present embodiment will be described in detail in connection with liquid reagent retaining portion 1005 as an example.

Figure 11:
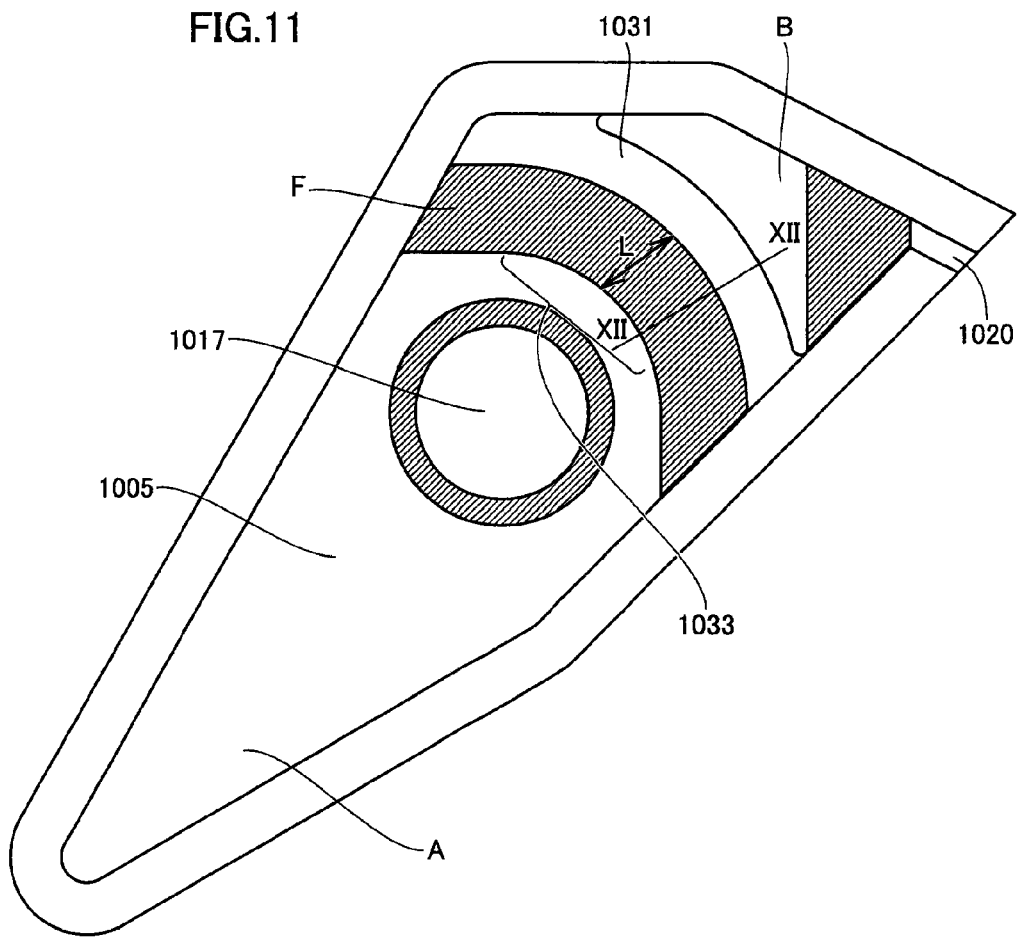
FIG. 11 is an enlarged top view of a liquid reagent retaining portion of the microchip shown in FIG. 10.
Figure 12:
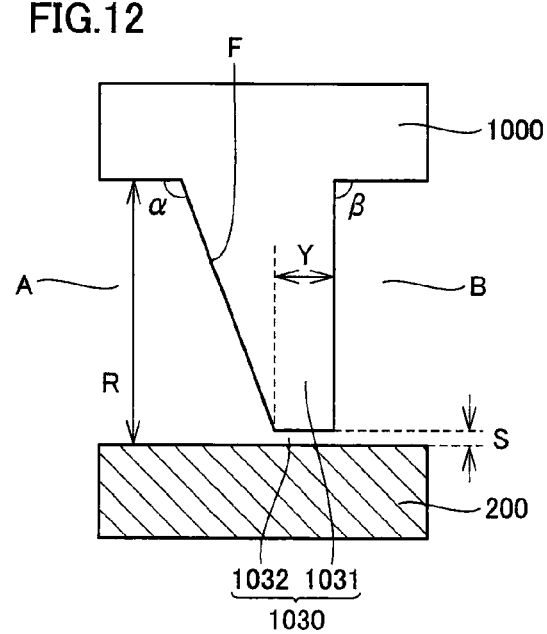
FIG. 12 is a schematic cross-sectional view along line XII-XII shown in FIG. 11.

FIG. 11 is an enlarged top view of liquid reagent retaining portion 1005 of the microchip shown in FIG. 10. FIG. 12 is a schematic cross-sectional view along line XII-XII shown in FIG. 11. FIG. 12 shows first substrate 1000 together with second substrate 200 bonded to first substrate 1000.

Liquid reagent retaining portion 1005 of the microchip shown in FIGS. 11 and 12 includes liquid reagent inlet 1017 composed of a through opening extending from a surface of the microchip (surface of first substrate 1000) to liquid reagent retaining portion 1005, and a reagent outlet 1020 serving as a fluid outlet for allowing liquid reagent R1 to flow out from liquid reagent retaining portion 1005. Liquid reagent retaining portion 1005 also includes a partition 1030 therein for dividing liquid reagent retaining portion 1005 into two sections, namely a first region A where the through opening forming liquid reagent inlet 1017 is provided and the liquid reagent is introduced and contained, and a second region B where reagent outlet 1020 is provided.

Partition 1030 as shown in FIG. 12 is formed by a protrusion 1031 provided on the second-substrate 200-side surface of first substrate 1000, and a communication gate 1032 formed by a space between the flat surface of the leading end of protrusion 1031 and the opposite surface (first-substrate 1000-side surface) of second substrate 200, for allowing communication between first region A and second region B.

As liquid reagent R1 is injected from liquid reagent inlet 1017 into liquid reagent retaining portion 1005 having the above-described structure, liquid reagent R1 is received in first region A. In the microchip having the above-described structure in which liquid reagent R1 is contained in first region A, liquid reagent R1 is less likely to flow out into second region B even if external impact is exerted or the internal pressure of first region A in liquid reagent retaining portion 1005 increases due to a change of the environmental temperature for example. Therefore, liquid reagent R1 contained in first region A can be effectively prevented from flowing out from liquid reagent retaining portion 1005. In other words, the liquid reagent retaining portion in the microchip of the present embodiment has an excellent reagent retaining ability against impact and an increase of the internal pressure of the liquid reagent retaining portion. While the liquid reagent retaining portion has a relatively simple structure, the liquid reagent retaining portion can effectively prevent unintended outflow of the liquid reagent from the liquid reagent retaining portion due to impact and the increase of the internal pressure of the liquid reagent retaining portion. Partition 1030 having communication gate 1032 has the function of "valve." If outflow is not desired, partition 1030 serves to keep liquid reagent R1 from flowing out from first region A. If outflow is desired, partition 1030 allows liquid reagent R1 to flow out from first region A by application of a centrifugal force with a predetermined strength.

In the microchip shown in FIGS. 11 and 12, reagent outlet 1020 also has the function of valve. Liquid reagent retaining portion 1005 therefore has the two-stage valve. Since reagent outlet 1020 thus has the valve function, even if impact is exerted to cause liquid reagent R1 to flow out from communication gate 1032 into second region B, the possibility that liquid reagent R1 flows out from liquid reagent retaining portion 1005 can be made extremely low.

Further, since partition 1030 is provided, when liquid reagent R1 is injected into liquid reagent retaining portion 1005, liquid reagent R1 can be suppressed or prevented from occupying the inside opening (opening abutting on first region A) of reagent outlet 1020. Further, liquid reagent R1 can be suppressed or prevented from moving due to impact to occupy the inside opening of reagent outlet 1020 as described above. It can therefore be suppressed or prevented that liquid reagent R1 occupying the inside opening is caused to flow out from the liquid reagent retaining portion due to an increase of the internal pressure in the liquid reagent retaining portion due to an increase of the environmental temperature, for example.

Here, a part of partition 1030 includes a curved portion 1033 formed of a wall in the shape of a curve as shown in FIG. 11, as seen from the surface of the microchip (the surface of first substrate 1000 for example) (namely when the microchip is seen from the upper surface side in the direction of thickness of the microchip). Specifically, protrusion 1031 forming partition 1030 includes arc-shaped curved portion 1033 at a central portion, and straight walls formed at the two opposing ends of curved portion 1033. Since the partition thus has a curved portion, when the liquid reagent in first region A is caused to contact the partition under a certain pressure (for example impact on the microchip or an increase of the internal pressure in first region A) for example, the pressure exerted by the liquid reagent can be dispersed. Further, in the case where the liquid reagent is a circular bulk, the contact area between the partition and the liquid reagent can be increased, so that the liquid-reagent-retaining capability can be further improved. In order to further improve the liquid-reagent-retaining capability, it is preferable that the partition having the curved portion protrudes toward second region B as shown in FIG. 11.

The shape of the curved portion is not particularly limited to a specific one. The curved portion is preferably arc-shaped, since the arc shape can more efficiently disperse the pressure and since the liquid reagent contained in the liquid reagent retaining portion is usually water-based reagent and forming a substantially circular bulk solution in the first region A. The curved portion in the shape of an arc can more efficiently disperse the pressure from the liquid reagent and can increase the contact area between the partition and the liquid reagent and therefore can further improve the liquid-reagent-retaining capability.

In the case where the curved portion has the shape of an arc, the radius of curvature of the arc is not particularly limited to a specific one, and may be approximately 2 to 5 mm for example. It is preferable that the radius of curvature is adjusted according to the amount of the liquid reagent contained in the liquid reagent retaining portion. Specifically, the radius of curvature of the arc is identical or substantially identical to the radius of the circular bulk solution shown by the liquid reagent in first region A.

Referring to FIG. 12, height S of communication gate 1032 is preferably approximately 0.1 to 0.2 mm. If height S is smaller than 0.1 mm, the first substrate and the second substrate could be welded together in the region where the communication gate is to be formed, in the process of manufacturing the microchip, and the liquid reagent may not flow out from first region A even when a centrifugal force is applied. If height S is larger than 0.2 mm, partition 1030 cannot have an appropriate valve function, so that the liquid reagent could be caused to flow out from first region A due to impact or increase of the internal pressure. Length Y of communication gate 1032 is not particularly limited to a specific one as long as partition 1030 can have an appropriate valve function, and may be approximately 0.2 to 2 mm and preferably approximately 0.5 to 1.0, for example. In order to discharge the liquid reagent without leaving the liquid when a centrifugal force is applied, preferably the flat surface at the leading end of protrusion 1031 and the opposite surface of second substrate 200 (first-substrate 1000-side surface) are preferably parallel or substantially parallel to each other.

Preferably, the side surface of partition 1030 that is located on first region A side has an inclined surface which is inclined with respect to the thickness direction of the microchip. Specifically, protrusion 1031 forming partition 1030 has an inclined surface F on first region A side as shown in FIGS. 11 and 12. Since such inclined surface F is provided, the whole amount of the liquid reagent can be smoothly flown out from first region A when a predetermined centrifugal force is applied for the purpose of causing the liquid reagent to flow out therefrom, and thus the liquid reagent can be prevented from remaining in first region A. The angle of inclination of inclined surface F, namely the angle formed by the surface of first substrate 1000 that forms first region A and inclined surface F (angle α in FIG. 12) is preferably an obtuse angle, and more preferably 95° or more. In contrast, the angle formed by the surface of first substrate 1000 that forms second region B and the side of protrusion 1031 on second region B side (angle β in FIG. 12) is not particularly limited to a specific one, and may be approximately 90° or an acute angle. Width L (see FIG. 11) of protrusion 1031 in the region where inclined surface F is formed is preferably set relatively long, since the liquid reagent retaining capability is further improved when the contact area where the liquid reagent contacts protrusion 1031 is larger. Width L may be approximately 1 to 3 mm for example.

The position of partition 1030 in liquid reagent retaining portion 1005 is not particularly limited to a specific one, as long as the partition is disposed between liquid reagent inlet 1017 and liquid reagent outlet 1020.

In liquid reagent retaining portions 1004 and 1006, similar partitions are provided as well (see FIG. 10), while which will not be described in detail. The partition provided in liquid reagent retaining portion 1006 is formed of a linear protrusion as seen from the surface of the microchip.

In the microchip shown in FIG. 10, liquid reagent container 1007 for temporarily containing liquid reagent R1 is provided adjacent to liquid reagent retaining portion 1005 retaining liquid reagent R1. Specifically, liquid reagent container 1007 is connected to an end of reagent outlet 1020 of liquid reagent retaining portion 1005, and is disposed in such a manner that liquid reagent R1 flowing out from liquid reagent retaining portion 1005 is temporarily contained in liquid reagent container 1007. Similarly, liquid reagent container 1008 is provided adjacent to liquid reagent retaining portion 1006.

Liquid reagent container 1007 includes an opening in addition to the one at the portion where liquid reagent container 1007 is connected to reagent outlet 1020. To the opening, liquid reagent measuring portion 1010 is connected. Thus, when a centrifugal force in an appropriate direction (leftward centrifugal direction with respect to FIG. 10 for example) is applied to cause liquid reagent R1 to be discharged from liquid reagent container 1007, liquid reagent R1 is introduced by the centrifugal force into liquid reagent measuring portion 1010 where the reagent is measured.

Since liquid reagent container 1007 capable of temporarily containing liquid reagent R1 which flows out from liquid reagent retaining portion 1005 is provided, even if liquid reagent R1 flows out from liquid reagent retaining portion 1005 due to impact on the microchip or an increase of the internal pressure of liquid reagent retaining portion 1005, liquid reagent R1 can be prevented from flowing out into liquid reagent measuring portion 1010. Further, in the case where the microchip contains therein a plurality of different liquid reagents, such a liquid reagent container can perform the function of temporarily keeping the liquid reagent on standby. Thus, each of the liquid reagents can be introduced at an appropriate timing into the measuring portion and can be mixed with a sample at an appropriate timing. The microchip having such a liquid reagent container is particularly useful in the case where a plurality of different liquid reagents have to be mixed with a sample successively in an appropriate order.

An operational method of the microchip shown in FIG. 10 will be generally described. Here, the operational method described below is an exemplary one, and is not limited to the method as described. First, a sample tube into which a sample of the whole blood is taken is inserted into sample tube mount portion 1001. Next, a centrifugal force in the leftward direction with respect to FIG. 10 (hereinafter simply referred to as leftward centrifugal force, centrifugal forces in other directions will be called similarly below) is applied to the microchip to draw out the whole-blood sample in the sample tube. After this, a downward centrifugal force is applied to cause the whole-blood sample to be introduced into separating portion 1002 where the blood is separated into a blood plasma component and a blood cell component by centrifugal separation. Next, a leftward centrifugal force is applied to remove the blood plasma component in the upper layer. At this time, the removed blood plasma component is contained in a region "a'." Subsequently, a downward centrifugal force is applied to smooth the surface of the blood cell component in separating portion 1002, and move the removed blood plasma component to a region "b'." Next, a rightward centrifugal force is applied to introduce liquid reagent R0 in liquid reagent retaining portion 1004 into liquid reagent measuring portion 1009 to measure the liquid reagent. This centrifugal force causes liquid reagent R1 in liquid reagent retaining portion 1005 and liquid reagent R2 in liquid reagent retaining portion 1006 to move to liquid reagent containers 1007 and 1008 respectively. This centrifugal force also causes the blood cell component in separating portion 1002 to be introduced into blood cell measuring portion 1003 and measured therein.

Next, a downward centrifugal force is applied to mix the measured blood cell component with liquid reagent R0 in first mixing portion 1012 to produce a liquid mixture. This centrifugal force causes liquid reagent R2 in liquid reagent container 1008 to be measured in liquid reagent measuring portion 1011. Then, rightward, downward, leftward and downward centrifugal forces are successively applied to sufficiently mix this liquid mixture. This leftward centrifugal force as applied allows liquid reagent R1 in liquid reagent container 1007 to be measured in liquid reagent measuring portion 1010. Further, the last downward centrifugal force causes the measured liquid reagent R1 to move to second mixing portion 1014.

Next, a leftward centrifugal force is applied and thereafter an upper-leftward centrifugal force and then a leftward centrifugal force are applied to introduce the supernatant portion of the liquid mixture in first mixing portion 1012 into liquid mixture measuring portion 1013 and measured therein. Then, a downward centrifugal force is applied to mix the measured liquid mixture with liquid reagent R1 in second mixing portion 1014. Subsequently, leftward and downward centrifugal forces are successively applied to sufficiently mix the liquid mixture. In the state where the downward centrifugal force is applied, the measured liquid reagent R2 is located in a region "c'." Next, a rightward centrifugal force is applied to mix the liquid mixture with liquid reagent R2 in detecting portion 1015. Further, a downward centrifugal force is applied to sufficiently mix the liquid mixture and the liquid reagent. Finally, a rightward centrifugal force is applied so that the liquid mixture is contained in detecting portion 1015. Light is applied to detecting portion 1015 and optical measurement is performed such as measurement of the intensity of the transmitted light, for example.

Figure 13:
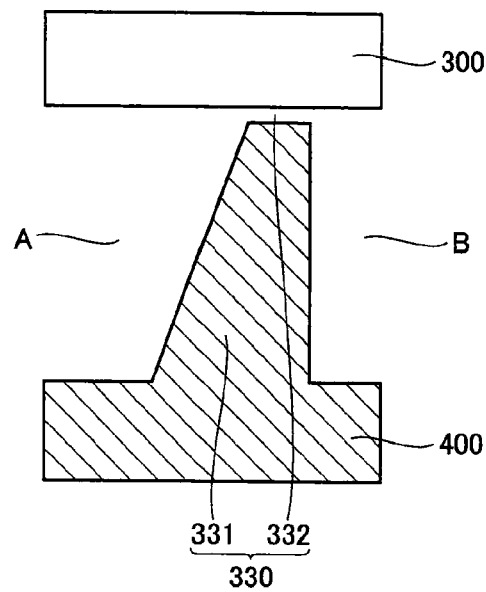
FIG. 13 is a schematic cross-sectional view showing another example of the liquid reagent retaining portion of the microchip according to the third embodiment of the present invention.

FIG. 13 is a schematic cross-sectional view showing another example of the liquid reagent retaining portion included in the microchip of the present embodiment. Like the liquid reagent retaining portion shown in FIGS. 11 and 12, the liquid reagent retaining portion of the microchip shown in FIG. 13 includes therein a partition 330 dividing the liquid reagent retaining portion into a first region A where a through opening forming the liquid reagent inlet is provided and a second region B where the reagent outlet is provided. Partition 330 is constituted of a protrusion 331 provided on the first-substrate 300-side surface of a second substrate 400, and a communication gate 332 formed by a space between a flat surface at the leading end of protrusion 331 and the opposite surface of a first substrate 300 (second-substrate 400-side surface), for allowing communication between first region A and second region B. As described above, the protrusion forming the partition may be provided on the second substrate.

Like the liquid reagent retaining portion shown in FIGS. 11 and 12, the flat surface at the leading end of protrusion 331 and the opposite surface of first substrate 300 (second-substrate 400-side surface) are preferably parallel or substantially parallel to each other.

Figure 14:
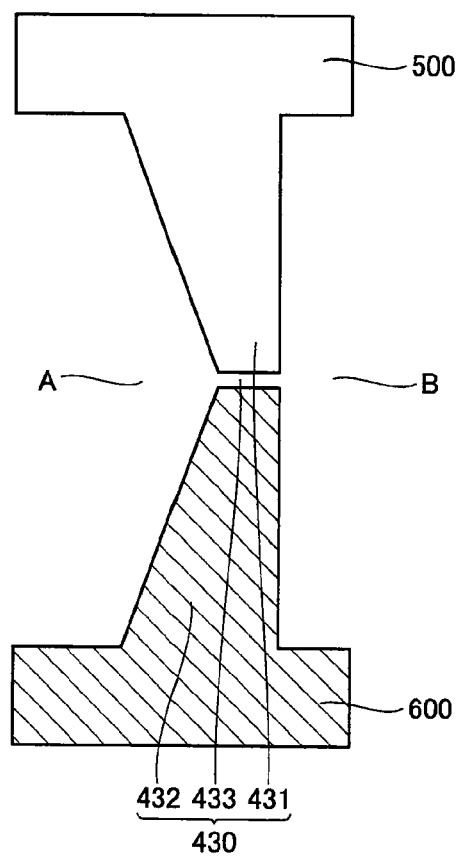
FIG. 14 is a schematic cross-sectional view showing still another example of the liquid reagent retaining portion of the microchip according to the third embodiment of the present invention.

FIG. 14 is a schematic cross-sectional view showing still another example of the liquid reagent retaining portion included in the microchip of the present embodiment. Like the liquid reagent retaining portion shown in FIGS. 11 and 12, the liquid reagent retaining portion of the microchip shown in FIG. 14 includes therein a partition 430 dividing the liquid reagent retaining portion into two regions, namely a first region A where a through opening forming the liquid reagent inlet is provided and a second region B where the reagent outlet is provided. Partition 430 is constituted of a protrusion 431 provided on a first substrate 500, a protrusion 432 provided on a second substrate 600 and a communication gate 433 formed by a space between a flat surface at the leading end of protrusion 431 and a flat surface at the leading end of protrusion 432, for allowing communication between first region A and second region B. As described above, respective protrusions forming the partition may be provided on both of the first substrate and the second substrate respectively and the communication gate may be disposed in (or near) the middle portion, instead of the ceiling or bottom of the liquid reagent retaining portion.

Like the liquid reagent retaining portion shown in FIGS. 11 and 12, the flat surface at the leading end of protrusion 431 and the flat surface at the leading end of protrusion 432 are preferably parallel or substantially parallel to each other. The angle formed by the surface of first substrate 500 that forms first region A and the first-region A-side side surface of protrusion 431 which is provided on the surface of first substrate 500 is preferably an obtuse angle, and more preferably 95° or more. Likewise, the angle formed by the surface of second substrate 600 that forms first region A and the first-region A-side side surface of protrusion 432 which is provided on the surface of the second substrate 600 is preferably an obtuse angle, and more preferably 95° or more.

Fourth Embodiment

A microchip of the present embodiment will be described in connection with a preferred example thereof. While characteristic features of the microchip of the present embodiment will be chiefly described below, other features are similar to those of the first embodiment as described above.

Figure 15:
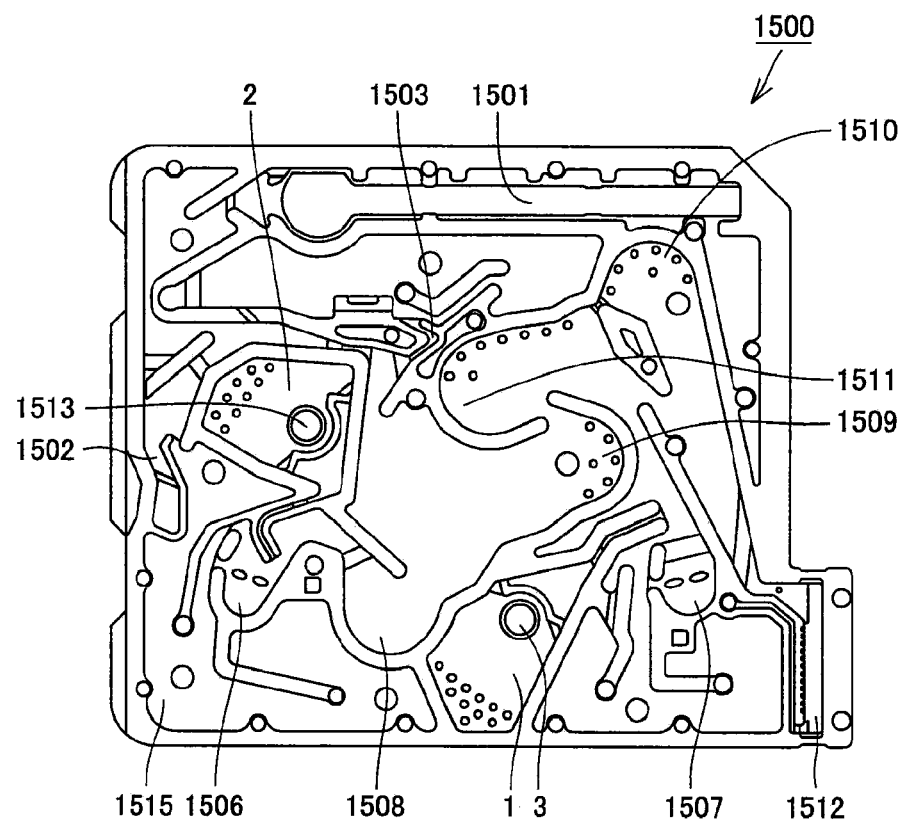
FIG. 15 is a plan view showing a preferred example of a first substrate having a groove formed in a surface and used for a microchip according to a fourth embodiment of the present invention.

FIG. 15 is a plan view showing a preferred example of a first substrate 1500 having a groove formed in a surface and used for the microchip of the present embodiment. FIG. 15 shows the groove-formed surface of first substrate 1500. The microchip of the present embodiment is formed by superposing and bonding first substrate 1500 on a second substrate (not shown) having an identical or similar outline form to first substrate 1500, in such a manner that the groove-formed surface of first substrate 1500 is located opposite to the second substrate. First substrate 1500 and the second substrate are respectively a plastic transparent substrate and a plastic black substrate, for example.

Referring to FIG. 15, the microchip of the present embodiment is chiefly constituted of a sample tube mount portion 1501 for incorporating a sample tube such as capillary containing the whole blood taken from a subject, a blood plasma separating portion 1502 for removing components such as blood cell from the whole blood drawn from the sample tube to obtain a blood plasma component, a sample measuring portion 1503 for measuring the separated blood plasma component, two liquid reagent retaining portions 1, 2 serving as fluid retaining reservoirs for retaining a liquid reagent, two liquid reagent measuring portions 1506, 1507 for measuring a liquid reagent, mixing portions 1508, 1509, 1510, and 1511 for mixing the blood plasma component with a liquid reagent, and a detecting portion 1512 where a test and an analysis are conducted for the resultant liquid mixture. The two liquid reagent retaining portions 1, 2 respectively include liquid reagent inlets 3, 1513 for injecting a liquid reagent therefrom. Liquid reagent inlets 3, 1513 are each a through opening extending through first substrate 1500 in the thickness direction.

Figure 16:
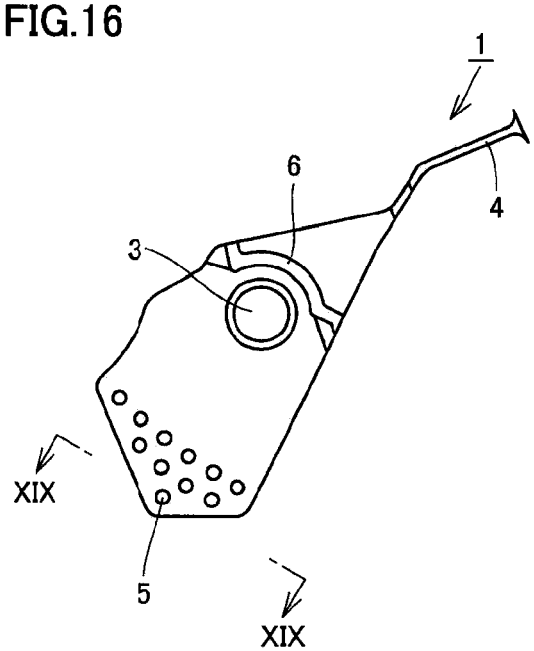
FIG. 16 is an enlarged plan view of a liquid reagent retaining portion of the first substrate shown in FIG. 15.

FIG. 16 is an enlarged plan view of liquid reagent retaining portion 1 in first substrate 1500 shown in FIG. 15. As shown in FIG. 16, liquid reagent retaining portion 1 includes a fluid outlet 4 for allowing the liquid reagent contained in the retaining portion to flow out. The end of the opening of fluid outlet 4 is made very small to such an extent sufficient to cause capillary action. This shape of the opening effectively suppresses unintended leakage of the liquid reagent from liquid reagent retaining portion 1.

Liquid reagent retaining portion 1 includes therein one or more columnar bodies 5 extending in the thickness direction of the microchip. Columnar body 5 is provided in a fluid retaining region where the farthest position from fluid outlet 4 in liquid reagent retaining portion 1 is included and a fluid is retained. "Fluid retaining region" refers to a region where a predetermined amount (may be the whole amount) of fluid (liquid reagent) introduced into a fluid containing reservoir (liquid reagent retaining portion) is located. The fluid is preferably retained as a mass by a surface tension or the like.

Figure 17:
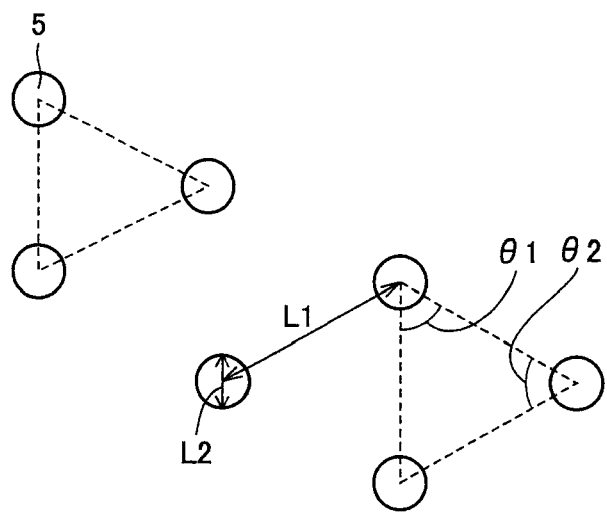
FIG. 17 is an enlarged diagram showing an arrangement of columnar bodies in the liquid reagent retaining portion shown in FIG. 16.
Figure 18:
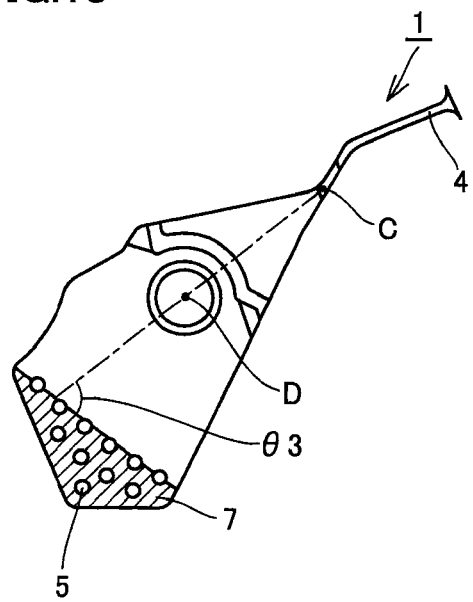
FIG. 18 is a plan view showing a relation between a plurality of columnar bodies in the liquid reagent retaining portion shown in FIG. 16 and a liquid reagent retained in the liquid reagent retaining portion.

FIG. 17 is an enlarged view showing an arrangement of columnar bodies 5 in liquid reagent retaining portion 1 shown in FIG. 16. FIG. 18 is a plan view showing a relation between a plurality of columnar bodies 5 in liquid reagent retaining portion 1 shown in FIG. 16 and the liquid reagent retained in liquid reagent retaining portion 1.

As shown in FIG. 17, liquid reagent retaining portion 1 shown in FIG. 16 includes three or more columnar bodies 5, and columnar bodies 5 are arranged in such a manner that each columnar body is located at a vertex position of a substantially regular triangle. Namely, in FIG. 17, columnar bodies 5 are each disposed to form a regular triangle with other adjacent columnar bodies 5. Here, length L1 of one side of the regular triangle is preferably 0.1 to 1 mm, and particularly preferably 0.5 to 1 mm. It is supposed here that "length of one side" refers to the distance between respective centers of a plurality of columnar bodies 5 as shown in FIG. 17. "Substantially regular triangle" is preferably a triangle having angles θ1 and θ2 in FIG. 17 of 60° each. However, "substantially regular triangle" here also includes a triangle where angles θ1 and θ2 are each 45 to 75°.

As a plurality of columnar bodies 5 are arranged to form a substantially regular triangle, tensile forces are uniformly exerted by columnar bodies 5 on the retained liquid reagent 7, so that liquid reagent 7 can be retained stably. Further, as a plurality of columnar bodies 5 are arranged to form a substantially regular triangle, the liquid reagent can be efficiently retained without excessively increasing the area occupied by the fluid retaining region.

Length L1 may be appropriately set to an optimum length according to the wettability (angle of contact) of the liquid reagent contained in liquid reagent retaining portion 1. Basically, however, a fluid (liquid reagent) with any angle of contact can be retained in the fluid retaining region as long as length L1 is 0.1 to 1 mm. In the liquid reagent retaining portion shown in FIG. 16, columnar bodies 5 are each arranged at a vertex position of a substantially regular triangle. The columnar bodies, however, may not be arranged in this manner. In this case, the distance between columnar bodies 5 is preferably 0.1 to 1 mm.

As shown in FIG. 18, it is preferable that liquid reagent retaining portion 1 includes two or more columnar bodies 5, and columnar bodies 5 are arranged on the liquid surface of liquid reagent 7 that is formed when the whole amount of liquid reagent 7 which is a fluid contained in liquid reagent retaining portion 1 is retained in the above-described fluid retaining region.

Specifically, an arrangement of two more columnar bodies 5 and the liquid surface of liquid reagent 7 in the fluid retaining region are made coincident with each other, so that the surface tension of liquid reagent 7 can be utilized to more efficiently retain liquid reagent 7 in the fluid retaining region. In the case where a plurality of columnar bodies 5 are arranged on the liquid surface (fluid surface) of liquid reagent 7, liquid reagent 7 is caught in the state of protruding from the portion between a plurality of columnar bodies 5 by the surface tension, and thus liquid reagent 7 is retained in the fluid retaining region. Columnar bodies 5 arranged on the liquid surface of liquid reagent 7 may be arranged in the shape of an arc of a circle whose center is the start point C of fluid outlet 4.

In liquid reagent retaining portion 1 shown in FIG. 16, a partition 6 is provided for dividing liquid reagent retaining portion 1 into two sections, namely a first region including liquid reagent inlet 3 and a second region including fluid outlet 4 (see FIG. 16). A similar partition is also provided in liquid reagent retaining portion 2.

Partition 6 has, at its two opposing ends, two communication gates respectively for allowing communication between the first region and the second region. When liquid reagent 7 is injected from liquid reagent inlet 3 into liquid reagent retaining portion 1 having partition 6, liquid reagent 7 contained in the first region is less likely to flow into the second region, even if impact is exerted on the microchip, since the two communication gates function as a valve. The region equally distant from the two communication gates maybe the above-described fluid retaining region. As described below, the microchip of the present embodiment includes columnar body 5 so that liquid reagent retaining portion 1 can be appropriately made in a desired shape.

The liquid reagent retaining portion in the microchip of the present embodiment has an excellent liquid reagent retaining capability against impact, so that unintended outflow of the liquid reagent from the liquid reagent retaining portion due to impact can be effectively suppressed or prevented. The valve function here means that undesired discharge of the liquid reagent is prevented, while desired discharge of the liquid reagent can be accomplished by application of a centrifugal force with a predetermined strength. In liquid reagent retaining portion 1 shown in FIG. 16, fluid outlet 4 also has the valve function. Therefore, liquid reagent retaining portion 1 is structured in such a manner that leakage of the liquid reagent to the outside is extremely unlikely to occur because of the synergetic effect provided by the three structures, namely columnar body 5, partition 6 and fluid outlet 4.

In liquid reagent retaining portion 1 shown in FIG. 16, it is preferable that liquid reagent inlet 3 is disposed between fluid outlet 4 and the fluid retaining region, and that two or more columnar bodies 5 are arranged in the direction substantially perpendicular to a straight line connecting fluid outlet 4 and a center D of liquid reagent inlet 3. It is also preferable that the outermost columnar bodies are located substantially perpendicular to a straight line connecting fluid outlet 4 and a center D of liquid reagent inlet 3. Here, "substantially perpendicular" refers to the state where angle θ3 shown in FIG. 18 is in a range of 60 to 120°. With this arrangement, outflow of liquid reagent 7 from fluid outlet 4 can be effectively suppressed.

The shape of columnar body 5 may be a circular cylinder as shown in FIG. 17, a column having a polygonal cross section, or a body tapering toward at least one end (such as cone, pyramid, fusiform body). Columnar body 5 may have a void or protrusion for example. In terms of easiness of molding, however, it is preferable to provide a columnar body of a circular cylinder in shape at the first substrate. Referring to FIG. 17, in the case where columnar body 5 is a circular cylinder, diameter L2 is preferably 0.3 to 1.5 mm, and particularly preferably 0.5 to 1.0 mm. When diameter L2 of columnar body 5 is in this range, the ability to retain liquid reagent 7 is further improved since the density of the arrangement of columnar bodies 5 and the area of contact between columnar bodies 5 and the fluid are appropriately set.

Figure 19:
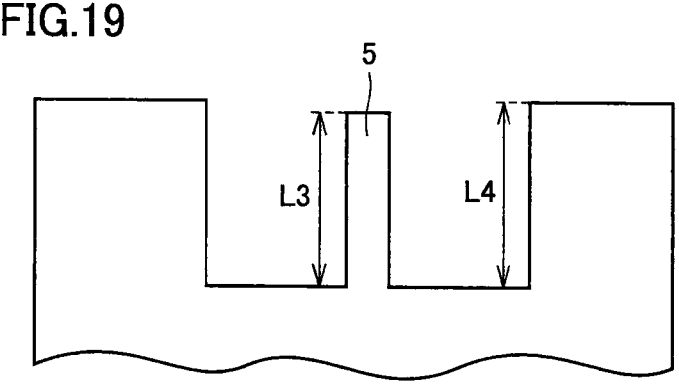
FIG. 19 is a cross-sectional view along line XIX-XIX shown in FIG. 16.

FIG. 19 is a cross sectional view along line XIX-XIX in FIG. 16. As shown in FIG. 19, length L3 of columnar body 5 in the thickness direction of the microchip is preferably substantially identical to depth L4 of the groove forming liquid reagent retaining portion 1. In the case where L3 and L4 are substantially equal to each other, particularly the surface tension of liquid reagent 7 can be used to the maximum extent to retain liquid reagent 7 in the fluid retaining region.

The difference between length L3 of columnar body 5 in the thickness direction of the microchip and depth L4 of the groove is preferably 0 to 0.5 mm and particularly preferably 0 to 0.1 mm. When the difference exceeds 0.5 mm, there is a possibility that liquid reagent 7 could not be retained in the fluid retaining region. In the case where a plurality of columnar bodies 5 are arranged, respective lengths L3 are preferably identical to each other. These lengths L3, however, may be different from each other.

While respective shapes (diameter L2, length L3) of columnar bodies 5 are preferably identical to each other in liquid reagent retaining portion 1, columnar bodies 5 having different shapes may be present in the same retaining portion.

Further, the liquid reagent retaining portion of the present embodiment may include, in addition to columnar bodies extending in the thickness direction of the microchip, a structural body extending perpendicularly to the thickness direction and connecting these columnar bodies. Namely, the columnar body of the present embodiment includes a mesh-like structural body as long as a columnar body extending in the thickness direction of the microchip is included. In the case where the mesh-like columnar body is provided, the ability to retain the liquid reagent can be further improved.

Figure 20:
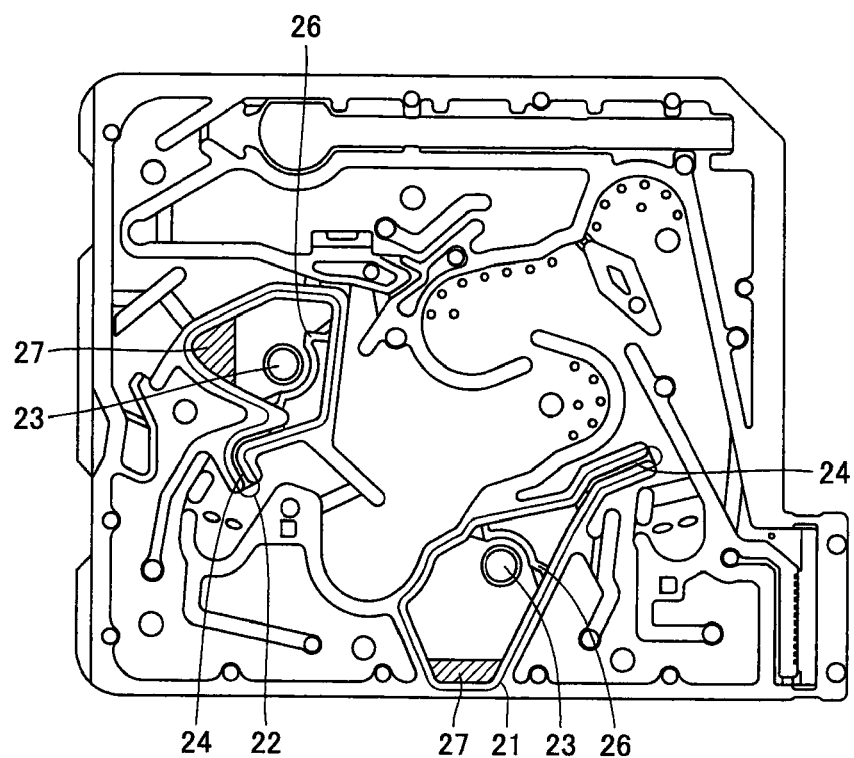
FIG. 20 is a plan view showing a microchip without columnar body.
Figure 21:
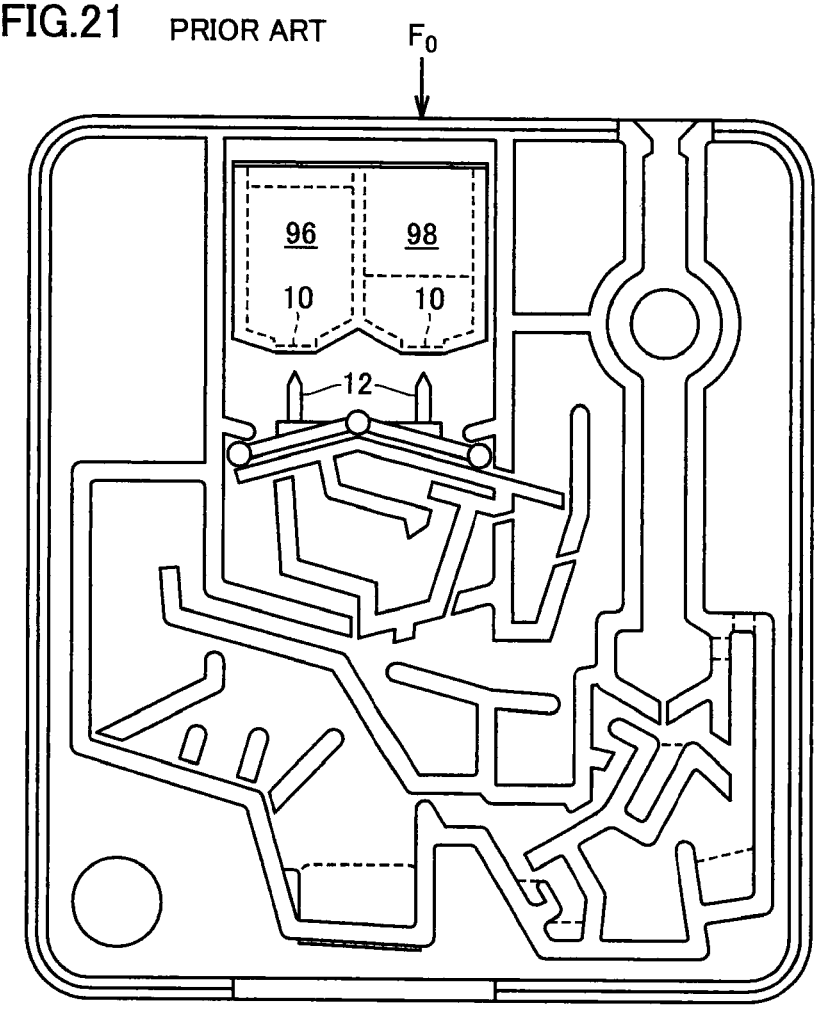
FIG. 21 is a plan view showing an example of a conventional reagent-contained microchip.

FIG. 20 is a plan view showing a microchip without columnar body, provided as a reference drawing relative to the microchip of the present embodiment.

The microchip shown in FIG. 20 includes liquid reagent retaining portions 21, 22, and liquid reagent retaining portions 21, 22 each include a fluid outlet 24, a liquid reagent inlet 23 and a partition 26. Liquid reagent retaining portions 21, 22 retain a liquid reagent 27. Since partition 26 is provided, movement of liquid reagent 27 toward fluid outlet 24 can be hindered to a certain degree.

In the microchip shown in FIG. 20 without columnar body, it is necessary to increase the area of contact between the inner wall surface of liquid reagent retaining portions 21, 22 and liquid reagent 27 as much as possible, in order to enhance the ability to retain the liquid reagent. In this case, the shape of liquid reagent retaining portions 21, 22 could be restricted in consideration of the contact area with liquid reagent 27.

In contrast, since the microchip of the present embodiment includes the columnar body, the shape of the liquid reagent retaining portion can be selected from a broader variety of different shapes. Accordingly, the form of the entire fluid circuit of the microchip can include a broader variety of different forms. As compared with the case where no columnar body is provided, the liquid reagent can be more firmly retained in the fluid retaining region of the liquid reagent retaining portion.

Here, the columnar body may be formed at any one of the first substrate and the second substrate. For example, the columnar body may be formed in a region corresponding to the liquid reagent retaining portion of the surface provided with the groove forming the fluid circuit of the first substrate, or the columnar body may be formed at a surface of the second substrate.

An operational method of the microchip shown in FIG. 15 will be generally described. Here, the operational method described below is an exemplary one, and is not limited to the method as described. First, a sample tube into which a sample of the whole blood is taken is inserted into sample tube mount portion 1501. Next, a centrifugal force in the leftward direction with respect to FIG. 15 (hereinafter simply referred to as leftward centrifugal force, centrifugal forces in other directions will be called similarly below) is applied to the microchip to draw out the whole-blood sample in the sample tube. After this, a downward centrifugal force is applied to cause the whole-blood sample to be introduced into blood plasma separating portion 1502 where the blood is separated into a blood plasma component and a blood cell component by centrifugal separation. When the whole blood sample is introduced into blood plasma separating portion 1502, some of the whole-blood sample overflowing from blood plasma separating portion 1502 is received in a waste liquid storage 1515. The downward centrifugal force also causes the liquid reagent retained in the fluid retaining region of liquid reagent retaining portion 2 to flow through the fluid outlet and to be introduced into liquid reagent measuring portion 1506 where the liquid reagent is measured.

Then, a rightward centrifugal force is applied to introduce the separated blood plasma component into sample measuring portion 1503. At this time, the measured liquid reagent is caused to move to mixing portion 1509, and the liquid reagent in liquid reagent retaining portion 1 is discharged from the fluid outlet.

Next, a downward centrifugal force is applied to mix the measured blood plasma component with the measured liquid reagent in mixing portion 1508, while the liquid reagent discharged from liquid reagent retaining portion 1 is measured in liquid reagent measuring portion 1507. Then, rightward, downward and rightward centrifugal forces are successively applied to cause the liquid mixture to flow between mixing portions 1508 and 1509, so that the liquid mixture is sufficiently mixed. Next, an upward centrifugal force is applied to mix the liquid mixture constituted of the liquid reagent and the blood plasma component, with the measured liquid reagent in mixing portion 1510. Then, leftward, upward, leftward and upward centrifugal forces are applied successively to move the liquid mixture between mixing portions 1510 and 1511 so that the liquid mixture is sufficiently mixed. Finally, a rightward centrifugal force is applied to introduce the liquid mixture in mixing portion 1510 into detecting portion 1512. Light is applied to detecting portion 1512 and optical measurement is performed on the liquid mixture in detecting portion 1512, such as measurement of the intensity of the transmitted light, for example.

EXAMPLES

In the following, the present invention will be described in more detail in connection with examples. The present invention, however, is not limited to these examples.

Example 1

A microchip was produced by bonding together a first substrate formed of a transparent plastic substrate and having the structure shown in FIGS. 1 and 2 and a second substrate that was a black substrate, by means of laser welding. All of the communication gates had a width of 0.3 mm. The bottom of the groove in the first substrate forming the upper inner wall of the communication gate was an inclined surface as shown in FIG. 4. Dimensions W4 and W5 shown in FIG. 4 were respectively 2.5 mm and 0.3 mm. Into liquid reagent retaining portions 104 and 105 of this microchip, 20 μL of a buffer fluid and 20 μL of a latex reagent were injected respectively, and thereafter a sealing label was attached to the surface of the microchip to seal liquid reagent inlets 113 and 114. Then, the microchip was wrapped with aluminum and further individually packaged in a paper box. Next, the packaged microchip was retained in a refrigerator for an hour at 8° C.

For the microchip immediately after taken out from the refrigerator, a free-fall impact test was conducted (five free falls from a height of 2 m to a floor of rubber mat). As a result, in none of the liquid reagent retaining portions, the liquid reagent flowed out into second region B.

Next, the microchip having undergone the impact test was retained in an environment of 25° C. for ten minutes to increase the internal pressure of the liquid reagent retaining portion (internal-pressure elevation test). As a result, although a slight amount of liquid reagent flowed out into second region B, most of the liquid reagent was retained in first region A.

Comparative Example 1

Ten microchips were produced similarly to Example 1 except that a first substrate without partition was used, and an impact test and an internal pressure elevation test were conducted. As a result of the impact test, it was found that, in all liquid reagent retaining portions of all microchips, the liquid reagent moved to close the inside opening of the outflow channel. Further, as a result of the internal pressure elevation test, in nine microchips out of the ten microchips, the liquid reagent in liquid reagent retaining portion 104 flowed out from the liquid reagent retaining portion. Similarly, in nine microchips out of the ten microchips, the liquid reagent in liquid reagent retaining portion 105 flowed out from the liquid reagent retaining portion.

Comparative Example 2

Ten microchips were produced and an impact test was performed similarly to Comparative Example 1 except that a pin hole was made in the sealing label on liquid reagent inlets 113 and 114 in order to prevent the internal pressure of the liquid reagent retaining portion from increasing due to a temperature increase. As a result, deterioration of the valve function of the outflow channel caused the liquid reagent in liquid reagent retaining portion 104 to flow out from the liquid reagent retaining portion in six microchips out of the ten microchips. Further, in ten microchips out of the ten microchips, the liquid reagent in liquid reagent retaining portion 105 flowed out from the liquid reagent retaining portion.

Example 2

A microchip was produced by bonding together a first substrate formed of a transparent plastic substrate having the structure shown in FIGS. 10, 11 and 12 and a second substrate that was a black substrate, by means of laser welding. Here, Height S of communication gate 1032 was 0.15 mm and length Y of communication gate 1032 was 0.6 mm. The depth of the liquid reagent retaining portion (depth: distance between first substrate 1000 and second substrate 200 in the liquid reagent retaining portion, corresponding to distance R in FIG. 12) was 2.8 mm. Curved portion 1033 was arc-shaped and the radius of curvature of the arc was 3.45 mm. The angle (angle α shown in FIG. 12) between the substrate surface forming first region A of first substrate 1000 and inclined surface F was 110°, and the angle (angle β in FIG. 12) between the substrate surface forming region B of first substrate 1000 and the side surface of protrusion 1031 on second region B side was 90°. Purified water was injected into liquid reagent retaining portion 1005 of the microchip, and thereafter a sealing label was attached to the surface of the microchip to seal liquid reagent inlet 1017. Then, the following evaluation tests were carried out.

(1) Evaluation of Fluid Operation

In the downward direction with respect to FIG. 10, a centrifugal force (3000 rpm, ten seconds) was applied, and thereafter a rightward centrifugal force (3000 rpm, ten seconds) was applied to introduce the purified water in liquid reagent retaining portion 1005 into liquid reagent container 1007. At this time, no liquid was left in liquid reagent retaining portion 1005.

(2) Fall Test

The microchip was caused to fall from a height of 2 m 20 times. As a result, the purified water did not flow out into second region B.

(3) Pressure Test

In an environment at a temperature of 4° C., the purified water in liquid reagent retaining portion 1005 was moved intentionally to contact partition 1030, and thereafter the microchip was left in a 37° C. environment for 20 minutes. While the internal pressure of first region A increased according to the temperature increase, the purified water did not flow out into second region B.

Although the present invention has been described and illustrated in detail, it is clearly understood that the same is by way of illustration and example only and is not to be taken by way of limitation, the scope of the present invention being interpreted by the terms of the appended claims.

What is claimed is:

1. A microchip comprising:
   a first substrate and a second substrate, said first substrate being superposed on and bonded to said second substrate and having a surface with a groove; and
   a fluid circuit composed of a cavity defined by said groove and a surface on said first substrate side of said second substrate, wherein
   said fluid circuit includes a fluid retaining reservoir for containing a liquid reagent,
   said first substrate has a fluid inlet for injecting the liquid reagent into said fluid retaining reservoir, said fluid inlet is a through opening extending through said first substrate from a surface opposite to said surface with the groove of said first substrate to said fluid retaining reservoir, and
   said fluid retaining reservoir includes:
      a fluid outlet or outflow channel for allowing the liquid reagent to flow out; and
      a partition dividing said fluid retaining reservoir into a first region including said fluid inlet and a second region including said fluid outlet or outflow channel, wherein said partition includes at least one communication gate for allowing communication between said first region and said second region, and
   wherein said fluid circuit further includes a measuring portion for measuring the liquid reagent that has been discharged from said fluid outlet or outflow channel.

2. The microchip according to claim 1, wherein
said partition includes two communication gates, and
said two communication gates are disposed respectively at two opposing ends of said partition.

3. The microchip according to claim 1, wherein
a cross section, parallel to said surface with the groove of said first substrate, of at least a part of said partition has a substantially V shape or substantially U shape protruding toward said first region.

4. The microchip according to claim 1, wherein
a cross section, parallel to said surface with the groove of said first substrate, of at least a part of said partition has a substantially V shape or substantially U shape protruding toward said second region.

5. The microchip according to claim 1, wherein
the height of said communication gate at an end abutting on said first region and the height of said communication gate at an end abutting on said second region are substantially equal to each other.

6. The microchip according to claim 1, wherein
said communication gate has an upper inner wall inclining in such a manner that the height of said communication gate decreases from said first region toward said second region.

7. The microchip according to claim 1, wherein
in said first region, a region adjacent to said communication gate has an upper inner wall inclining in such a manner that, in said region adjacent to said communication gate, the height of said fluid retaining reservoir decreases toward said communication gate.

8. The microchip according to claim 1, wherein said fluid outlet or outflow channel and said measuring portion are connected via a flow channel.

9. The microchip according to claim 1, wherein a capacity of said measuring portion is smaller than a capacity of said fluid retaining reservoir.

* * * * *